United States Patent
Hah

(10) Patent No.: US 9,540,348 B2
(45) Date of Patent: Jan. 10, 2017

(54) IMIDAZOLE-1-YL PYRIMIDINE DERIVATIVES, OR PHARMACUTICALLY ACCEPTABLE SALT THEREOF, AND PHARMACEUTIC COMPOSITION COMPRISING THE SAME AS AN ACTIVE INGREDIENT

(71) Applicant: Industry-University Cooperation Foundation Hanyang University ERICA Campus, Ansan (KR)

(72) Inventor: Jung-Mi Hah, Seoul (KR)

(73) Assignee: INDUSTRYUNIVERSITY COOPERATION FOUNDATION HANYANG UNIVERSITY ERICA CAMPUS, Ansansi (KR)

( * ) Notice: Subject to any disclaimer, the term of this patent is extended or adjusted under 35 U.S.C. 154(b) by 0 days.

(21) Appl. No.: 14/713,037

(22) Filed: May 15, 2015

(65) Prior Publication Data
US 2016/0200706 A1   Jul. 14, 2016

(30) Foreign Application Priority Data
Jan. 8, 2015   (KR) .................. 10-2015-0002907

(51) Int. Cl.
| | |
|---|---|
| *B65D 25/20* | (2006.01) |
| *B65D 83/00* | (2006.01) |
| *C07D 403/04* | (2006.01) |
| *C07D 403/14* | (2006.01) |
| *C07D 401/14* | (2006.01) |
| *C07D 405/14* | (2006.01) |

(52) U.S. Cl.
CPC ........... *C07D 403/04* (2013.01); *C07D 401/14* (2013.01); *C07D 403/14* (2013.01); *C07D 405/14* (2013.01)

(58) Field of Classification Search
CPC ................................ B65D 25/20; B65D 83/00
See application file for complete search history.

(56) References Cited

U.S. PATENT DOCUMENTS
2005/0282826 A1   12/2005 Malamas

FOREIGN PATENT DOCUMENTS
KR   10-1123071   2/2012

OTHER PUBLICATIONS

Design, synthesis and biological evaluation of benzyl 2-(1H-imidazole-1-yl) pyrimidine analogues as selective and potent Raf inhibitors Minjung Kim et al., Bioorganic & Medicinal Chemistry Letters, 24 (2014), pp. 3600-3604.*
Avruch, J.et al., "Ras Activation of the Raf Kinase: Tyrosine Kinase Recruitment of the MAP Kinase Cascade", Recent Prog. Horm. Res., Jan. 2001, vol. 56, pp. 127-155.
Khazak, V.; Astsaturov, I.; Serebriiskii, I. G.; Golemis, E. A., "Selective Raf Inhibition in Cancer Therapy", Expert. Opin. Ther. Targets, Dec. 2007, 11(12), pp. 1587-1609.
Wellbrock, C.; Karasarides, M.; Marais, R., "The Raf Proteins Take Centre Stage", Nat. Rev. Mol. Cell. Biol., Nov. 2004, vol. 5, pp. 875-885.
O'Neill, E.; Kolch, W., "Conferring specificity on the ubiquitous Raf/MEK signalling pathway", Br. J. Cancer, Jan. 20, 2004, 90, pp. 283-288.
Martelli, A. M. et al., "Roles of the Ras/Raf/MEK/ERK pathway in leukemia therapy" Leukemia, Apr. 15, 2011, 25, pp. 1080-1094.
Chappell, W. H. et al., "Ras/Raf/MEK/ERK and PI3K/PTEN/Akt/mTOR Inhibitors: Rationale and Importance to Inhibiting These Pathways in Human Health", Oncotarget, Mar. 11, 2011, vol. 2, pp. 135-164.
Garnett, M. J.; Marais, R., "Guilty as charged: B-RAF is a human oncogene", Cancer Cell, Oct. 2004, vol. 6, pp. 313-319.
Dumaz, N. et al., "In Melanoma, RAS Mutations Are Accompanied by Switching Signaling from BRAF to CRAF and Disrupted Cyclic AMP Signaling", Cancer Res. Oct. 2006, 1;66(19), pp. 9483-9491.
Kim, M.-H. et al., "Structure based design and syntheses of amino-1H-pyrazole amide derivatives as selective Raf kinase inhibitors in melanoma cells", Bioorg. Med. Chem., Feb. 3, 2011, 19, pp. 1915-1923.
Chen, J. et al., "Raf-1 promotes cell survival by antagonizing apoptosis signal-regulating kinase 1 through a MEK-ERK independent mechanism", Proc. Natl. Acad. Sci. U.S.A., May 4, 2001, 98, pp. 7783-7788.
A. von Gise et al, "Apoptosis Suppression by Raf-1 and MEK1 Requires MEK- and Phosphatidylinositol 3-Kinase-Dependent Signals", Mol. Cell Biol., Apr. 2001, 21, pp. 2324-2336.
Dumaz, N. et al., "In Melanoma, RAS Mutations Are Accompanied by Switching Signaling from BRAF to CRAF and Disrupted Cyclic AMP Signaling", Cancer Res., Oct. 1, 2006, 66, pp. 9483-9491.
Dhomen, N.; Marais, R., "New insight into BRAF mutations in cancer", Curr. Opin. Genet. Dev., Feb. 2007, 17, pp. 31-39.
Lee, J. et al., "Discovery and initial SAR of pyrimidin-4-yl-1H-imidazole derivatives with antiproliferative activity against melanoma cell lines", Bioorg. Med. Chem. Lett., Mar. 1, 2010, 20, pp. 1573-1577.
Minjung Kim et al., "Design, synthesis and biological evaluation of benzyl 2-(1H-imidazole-1-yl) pyrimidine analogues as selective and potent Raf inhibitors", Bioorganic & Medicinal Chemistry Letters 24, May 17, 2014, pp. 3600-3604.*

* cited by examiner

*Primary Examiner* — Ebenezer O Sackey
(74) *Attorney, Agent, or Firm* — Lex IP Meister, PLLC

(57) ABSTRACT

The present invention relates to a novel imidazole-1-yl pyrimidine derivative, a pharmaceutically acceptable salt thereof, and a pharmaceutic composition comprising the same. Since the imidazole-1-yl pyrimidine derivative according to the present invention shows the inhibition activity selectively to BRAF, BRAF mutants, or CRAF, it can be used to a pharmaceutic composition for preventing or treating cancer.

6 Claims, No Drawings

IMIDAZOLE-1-YL PYRIMIDINE DERIVATIVES, OR PHARMACUTICALLY ACCEPTABLE SALT THEREOF, AND PHARMACEUTIC COMPOSITION COMPRISING THE SAME AS AN ACTIVE INGREDIENT

BACKGROUND OF THE INVENTION (a) Field of the Invention

The present invention relates to imidazole-1-yl pyrimidine derivatives or a pharmaceutically acceptable salts thereof, and a pharmaceutic composition comprising the same as an active ingredient.

(b) Description of the Related Art

In spite of profound progress in cancer researches over the years, it is still the second leading cause of death worldwide. Extensive studies of the molecular mechanism of cancer have revealed many specific molecular targets for its therapy. In fact, the targeted cancer therapy has been very successful, particularly, in the case of kinase inhibitors. Protein kinases are involved in various cell signaling pathways including cell cycle regulation, apoptosis, and proliferation, and the dysregulation of specific protein kinases has been implicated in several cancers.

For example, in the case of melanoma, MAPK (mitogen-activated protein kinase; RAS-RAF-MEK-ERK) and PI3K-AKR (phosphoinositide 3-kinase-AKT) pathways are upregulated and alternation of the signaling through both the pathways plays a major role in melanoma progression.

Since the findings that about 70% of melanoma have V600E mutant, there have been significant amounts of small molecule inhibitors developed, which target BRAF V600E.

The recent success of Vemurafenib shows the importance of selective BRAF V600E inhibitor. Furthermore, there is a significant portion of melanomas (>33%) not including BRAF V600E mutations, which will require alternative therapy targets. CRAF (or RAF1) gene which is closely related to BRAF, is involved in abnormal proliferation of melanoma. Similar to BRAF, CRAF is involved in activating of a MAPK signal transduction system, but, unlike BRAF, CRAF controls lower proteins such as MST (STK3) and ASK1 (MAP3K5), independent of the MAPK signal transduction system.

Moreover, CRAF affects mitochondria directly, thereby controlling the inhibition of apoptosis, which is achieved via phosphorylation of BAD through direct coupling with BCL2. CRAF seems to be related with mutants of NRAS. A recent study, which shows that BRAF can directly phosphorylate CRAF, emphasizes the value of CRAF as a target protein for melanoma therapeutics. Therefore, the development of potent and selective CRAF inhibitors, as well as BRAF V600E inhibitors, would be ideal for melanoma treatment.

Known protein kinase inhibitors can be classified into type I and type II, depending on the conformational state of the kinase with the inhibitors bound. The type I inhibitors bind to the ATP-binding site through the formation of hydrogen bonds at the hinge region. Meanwhile, the type II inhibitor bind to the ATP-binding site, but also occupy the unique secondary hydrophobic pocket in the inactive conformation of the kinase domain. In this respect, the approach to the type II inhibitors may be stronger for the selective protein kinase inhibitor.

SUMMARY OF THE INVENTION

It is an object of the present invention to provide a novel imidazole-1-yl pyrimidine derivative exhibiting selective inhibition activity to protein kinases, or a pharmaceutically acceptable salt thereof.

It is another object of the present invention to provide a pharmaceutic composition for preventing or treating cancer comprising the imidazole-1-yl pyrimidine derivative or the pharmaceutically acceptable salt thereof as an active ingredient.

To achieve the objects, the present invention provides an imidazole-1-yl pyrimidine derivatives represented by the following Chemical Formula 1, or a pharmaceutically acceptable salt thereof, as one aspect.

[Chemical Formula 1]

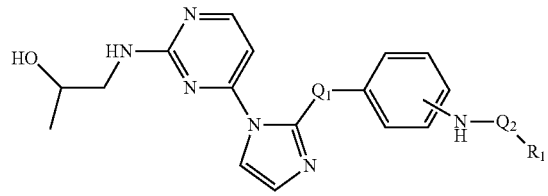

In Chemical Formula 1,
$Q_1$ is —$CH_2$— or —CO—;
$Q_2$ is —CO— or —CONH—;
$R_1$ is a $C_6$-$C_{20}$ aryl, a $C_7$-$C_{20}$ alkylaryl, a $C_7$-$C_{20}$ arylalkyl, a $C_5$-$C_{20}$ heteroaryl, a $C_3$-$C_{20}$ cycloalkyl, or a $C_3$-$C_{20}$ heterocycloalkyl, wherein said $R_1$ is substituted with a halogen, a halogenated alkyl, hydroxyl group, carbonyl group, cyano group, alkoxy group, or a $C_3$-$C_{20}$ heterocycloalkyl or not.

Furthermore, the present invention provides the imidazole-1-yl pyrimidine derivative represented by Chemical Formula 1 or the pharmaceutically acceptable salt thereof, and a pharmaceutic composition for preventing or treating cancer comprising the same, as other aspects.

The novel imidazole-1-yl pyrimidine derivative or the pharmaceutically acceptable salt thereof according to the present invention shows selective inhibition activity to various protein kinases and suppress the proliferation of abnormal cells, and particularly shows high inhibition rate to BRAF, BRAF mutants (for example, BRAF V599E, BRAF V600E and so on), or CRAF and can be used to the pharmaceutic composition for preventing or treating cancer such as melanoma and the like.

DETAILED DESCRIPTION OF THE EMBODIMENTS

In the present invention, the terms "the first", "the second", and the like are used for explaining various components and said terms are only used for distinguishing one component from the other components.

Furthermore, the terms used in this description are just for explaining exemplary examples and it is not intended to restrict the present invention. The singular expression may include the plural expression unless it is differently expressed contextually. It must be understood that the terms such as "include", "comprise", and "have" in the present description are only used for designating the existence of characteristics taken effect, numbers, steps, components, or combinations thereof, and do not exclude the existence or the possibility of addition of one or more different characteristics, numbers, steps, components of combinations thereof beforehand.

The present invention can be variously modified and have various examples, and specific examples of the present invention are explained in this description. However, it is not intended to limit the present invention to the specific examples and it must be understood that the present invention includes every modifications, equivalents, or replacements included in the idea and technical scope of the present invention.

Hereinafter, the present invention is explained in more detail.

There were previous studies of synthesizing a novel series of pyrimidine-4-yl-1H-imidazole-2-yl derivatives showing antiproliferative activity against melanoma cell line. Further assessment of the inhibitory acivity showed that the most potent compound on A375P can be very potent BRAF mutant inhibitor. The same compound also has good potency on wild-type BRAF.

The inventors of the present invention compared the active site of wild-type BRAF and BRAF mutants (for example, BRAF V599E, BRAF V600E and so on) through molecular docking studies and invented the derivative compound of the present invention on the basis of the fact that the activity and the selectivity of the imidazole derivative can be markedly increased when methylene/carbonyl moieties are introduced thereinto.

According to one embodiment of the present invention, an imidazole-1-yl pyrimidine derivative or a pharmaceutically acceptable salt thereof is provided.

Hereinafter, the imidazole-1-yl pyrimidine derivative is explained in more detail.

The imidazole-1-yl pyrimidine derivative according to one embodiment of the present invention is represented by the following Chemical Formula 1.

[Chemical Formula 1]

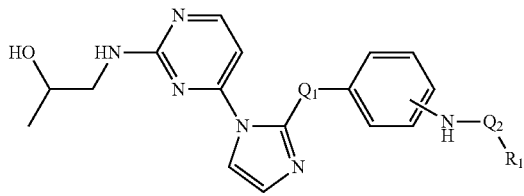

In Chemical Formula 1,
$Q_1$ is —$CH_2$— or —CO—;
$Q_2$ is —CO— or —CONH—;
$R_1$ is a $C_6$-$C_{20}$ aryl, a $C_7$-$C_{20}$ alkylaryl, a $C_7$-$C_{20}$ arylalkyl, a $C_5$-$C_{20}$ heteroaryl, a $C_3$-$C_{20}$ cycloalkyl, or a $C_3$-$C_{20}$ heterocycloalkyl, wherein said $R_1$ is substituted with a halogen, a halogenated alkyl, hydroxyl group, carbonyl group, cyano group, alkoxy group, or a $C_3$-$C_{20}$ heterocycloalkyl or not.

Compared to previous known compounds, the imidazole-1-yl pyrimidine derivative of the present invention is increased in the flexibility of the molecular structure due to methylene group or carbonyl group positioned between pyrimidine and imidazole. Accordingly, the tail moiety of the derivative compound can more easily approach to the secondary hydrophobic pocket and the compound can act as the type II inhibitor. Particularly, it can act as more potent and selective inhibitor against wild-type BRAF and BRAF mutants (for example, BRAF V599E, BRAF V600E and so on) kinase and CRAF kinase.

More specifically, each substituent in Chemical Formula 1 may be defined as follows.

Aryl means a monovalent monocyclic, bicyclic or tricyclic aromatic hydrocarbon part of 6 to 20 membered carbon ring, preferably 6 to 15 membered carbon ring, and it includes the compounds in which 2 or more aromatic hydrocarbons are connected.

Alkylaryl means the aryl group defined above of which one or more hydrogen atoms are substituted with an alkyl group.

Arylalkyl means the alkyl group defined above of which one or more hydrogen atoms are substituted with an aryl group.

Cycloalkyl means a saturated or unsaturated non-aromatic monovalent monocyclic, bicyclic or tricyclic aromatic hydrocarbon part of 3 to 20 membered carbon ring, preferably 3 to 12 membered carbon ring.

Heterocycloalkyl means the cycloalkyl defined above of which carbon atom is substituted with one or more heteroatoms.

Heteroaryl means the aryl defined above of which carbon atom is substituted with one or more hetero atoms.

Alkoxy means a linear or branched saturated monovalent hydrocarbon having 1 to 10 carbon atoms, preferably 1 to 6 carbon atoms, which is combined with oxygen by a single bond.

Heteroatom means the atom except carbon and hydrogen.

According to one embodiment of the present invention, $R_1$ may be chlorophenyl, dichlorophenyl, fluorophenyl, dimethylphenyl, quinolinyl, pyridinyl, pyrazinyl, 1H-benzotriazol-5-yl, biphenyl-2-yl, biphenyl-4-yl, trifluoromethylphenyl, bis(4-chlorophenyl)methyl, 2-chloro-5-(4-chlorobenzyl)phenyl, biphenyl-4-yl-methyl, 1-acetylpiperidin-4-yl, 5-(4-methoxyphenyl)furan-2-yl, 2-[(2-cyanophenyl)sulfanyl]phenyl, 6-hydroxy-2,5,7,8-tetramethyl-3,4-dihydro-2H-chromen-2-yl, bis(4-chlorophenyl)methyl, 4-(morpholin-4-yl)-3-(trifluoromethyl)phenyl, 3-(morpholin-4-yl)-4-(trifluoromethyl)phenyl, 3-(morpholin-4-yl)-5-(trifluoromethyl)phenyl, 1H-indol-3-yl-methyl, dihydro-1H-indol-2-yl, 3-chloro-4-(trifluoromethyl)phenyl, 3-(4-methylpiperazin-1-yl)-5-(trifluoromethyl)phenyl, 4-[(4-ethylpiperazin-1-yl)methyl]-3-(trifluoromethyl)phenyl, 3-(4-methylpiperazin-1-yl)-5-(trifluoromethyl)phenyl, and so on, but the present invention is not limited to or by them.

The representative compounds of Chemical Formula 1 according to the present invention may be as follows but the present invention is not limited to or by them:

(S)—N-(3-((1-(2-((2-hydroxypropyl)amino)pyrimidin-4-yl)-1H-imidazol-2-yl)methyl)phenyl)-3-(4-methylpiperazin-1-yl)-5-(trifluoromethyl)benzamide, (S)—N-(3-((1-(2-((2-hydroxypropyl)amino)pyrimidin-4-yl)-1H-imidazol-2-yl)methyl)phenyl)-3,5-dimethylbenzamide, (S)—N-(4-((1-(2-((2-hydroxypropyl)amino)pyrimidin-4-yl)-1H-imidazol-2-yl)methyl)phenyl)pyrazine-2-carboxamide, (S)-2-(2-fluorophenyl)-N-(3-((1-(2-((2-hydroxypropyl)amino)pyrimidin-4-yl)-1H-imidazol-2-yl)methyl)phenyl)acetamide, (S)—N-(3-((1-(2-((2-hydroxypropyl)amino)pyrimidin-4-yl)-1H-imidazol-2-yl)methyl)phenyl)-1-phenyl-5-(trifluoromethyl)-1H-pyrazole-4-carboxamide, (S)-4-chloro-N-(3-((1-(2-((2-hydroxypropyl)amino)pyrimidin-4-yl)-1H-imidazol-2-yl)methyl)phenyl)benzamide, (S)—N-(3-((1-(2-((2-hydroxypropyl)amino)pyrimidin-4-yl)-1H-imidazol-2-yl)methyl)phenyl)quinoline-2-carboxamide, (S)—N-(3-((1-(2-((2-hydroxypropyl)amino)pyrimidin-4-yl)-1H-imidazol-2-yl)methyl)phenyl)-1H-indole-3-carboxamide,
(S)—N-(3-((1-(2-((2-hydroxypropyl)amino)pyrimidin-4-yl)-1H-imidazol-2-yl)methyl)phenyl)isonicotinamide,
(S)—N-(3-((1-(2-((2-hydroxypropyl)amino)pyrimidin-4-yl)-1H-imidazol-2-yl)methyl)phenyl)-1H-benzo[d][1,2,3]triazole-5-carboxamide,
(S)-2-([1,1'-biphenyl]-4-yl)-N-(3-((1-(2-((2-hydroxypropyl)amino)pyrimidin-4-yl)-1H-imidazol-2-yl)methyl)phenyl)acetamide,
(S)—N-(3-((1-(2-((2-hydroxypropyl)amino)pyrimidin-4-yl)-1H-imidazol-2-yl)methyl)phenyl)-[1,1'-biphenyl]-4-carboxamide,
(S)—N-(3-((1-(2-((2-hydroxypropyl)amino)pyrimidin-4-yl)-1H-imidazol-2-yl)methyl)phenyl)-[1,1'-biphenyl]-2-carboxamide,
(S)-1-acetyl-N-(3-((1-(2-((2-hydroxypropyl)amino)pyrimidin-4-yl)-1H-imidazol-2-yl)methyl)phenyl)piperidine-4-carboxamide,
(S)-2-((2-cyanophenyl)thio)-N-(3-((1-(2-((2-hydroxypropyl)amino)pyrimidin-4-yl)-1H-imidazol-2-yl)methyl)phenyl)benzamide,
(R)-6-hydroxy-N-(3-((1-(2-(((S)-2-hydroxypropyl)amino)pyrimidin-4-yl)-1H-imidazol-2-yl)methyl)phenyl)-2,5,7,8-tetramethylchromane-2-carboxamide,
(S)-2-chloro-5-(4-chlorobenzyl)-N-(3-((1-(2-((2-hydroxypropyl)amino)-pyrimidin-4-yl)-1H-imidazol-2-yl)methyl)phenyl)benzamide,
(S)-2,2-bis(4-chlorophenyl)-N-(3-((1-(2-(2-hydroxypropylamino)pyrimidin-4-yl)-1H-imidazol-2-yl)methyl)phenyl)acetamide,
(S)—N-(3-((1-(2-((2-hydroxypropyl)amino)pyrimidin-4-yl)-1H-imidazol-2-yl)methyl)phenyl)-3-morpholino-2-(trifluoromethyl)benzamide,
(S)-4-chloro-N-(3-((1-(2-((2-hydroxypropyl)amino)pyrimidin-4-yl)-1H-imidazol-2-yl)methyl)phenyl)-3-(trifluoromethyl)benzamide,
(S)—N-(3-((1-(2-((2-hydroxypropyl)amino)pyrimidin-4-yl)-1H-imidazol-2-yl)methyl)phenyl)-3-morpholino-5-(trifluoromethyl)benzamide,
(S)-1-(3-chlorophenyl)-3-(3-((1-(2-((2-hydroxypropyl)amino)pyrimidin-4-yl)-1H-imidazol-2-yl)methyl)phenyl)urea,
(S)-1-(3,4-dichlorophenyl)-3-(3-((1-(2-((2-hydroxypropyl)amino)pyrimidin-4-yl)-1H-imidazol-2-yl)methyl)phenyl)urea,
(S)-1-(3-chloro-4-(trifluoromethyl)phenyl)-3-(3-((1-(2-((2-hydroxypropyl)amino)pyrimidin-4-yl)-1H-imidazol-2-yl)methyl)phenyl)urea,
(S)-1-(3-((4-ethylpiperazin-1-yl)methyl)-5-(trifluoromethyl)phenyl)-3-(3-((1-(2-((2-hydroxypropyl)amino)pyrimidin-4-yl)-1H-imidazol-2-yl)methyl)phenyl)urea,
(S)—N-(3-(1-(2-((2-hydroxypropyl)amino)pyrimidin-4-yl)-1H-imidazole-2-carbonyl)phenyl)-3-(trifluoromethyl)benzamide,
(S)—N-(3-(1-(2-((2-hydroxypropyl)amino)pyrimidin-4-yl)-1H-imidazole-2-carbonyl)phenyl)-5-(4-methoxyphenyl)furan-2-carboxamide,
(S)—N-(3-(1-(2-((2-hydroxypropyl)amino)pyrimidin-4-yl)-1H-imidazole-2-carbonyl)phenyl)-3-morpholino-5-(trifluoromethyl)benzamide,
(S)—N-(3-(1-(2-((2-hydroxypropyl)amino)pyrimidin-4-yl)-1H-imidazole-2-carbonyl)phenyl)-3-(4-methylpiperazin-1-yl)-5-(trifluoromethyl)benzamide,
(S)-4-chloro-N-(3-(1-(2-((2-hydroxypropyl)amino)pyrimidin-4-yl)-1H-imidazole-2-carbonyl)phenyl)benzamide,
(S)-3-chloro-N-(3-(1-(2-((2-hydroxypropyl)amino)pyrimidin-4-yl)-1H-imidazole-2-carbonyl)phenyl)benzamide,
(S)-1-(3,4-dichlorophenyl)-3-(3-(1-(2-((2-hydroxypropyl)amino)pyrimidin-4-yl)-1H-imidazole-2-carbonyl)phenyl)urea,
(S)-1-(4-chlorophenyl)-3-(3-(1-(2-((2-hydroxypropyl)amino)pyrimidin-4-yl)-1H-imidazole-2-carbonyl)phenyl)urea,
(S)-4-chloro-N-(4-(1-(2-((2-hydroxypropyl)amino)pyrimidin-4-yl)-1H-imidazole-2-carbonyl)phenyl)benzamide,
(S)-3-chloro-N-(4-(1-(2-((2-hydroxypropyl)amino)pyrimidin-4-yl)-1H-imidazole-2-carbonyl)phenyl)benzamide,
(S)—N-(4-(1-(2-((2-hydroxypropyl)amino)pyrimidin-4-yl)-1H-imidazole-2-carbonyl)phenyl)-3-morpholino-5-(trifluoromethyl)benzamide,
(S)-4-chloro-N-(4-(1-(2-((2-hydroxypropyl)amino)pyrimidin-4-yl)-1H-imidazole-2-carbonyl)phenyl)-3-(trifluoromethyl)benzamide,
(S)—N-(4-(1-(2-((2-hydroxypropyl)amino)pyrimidin-4-yl)-1H-imidazole-2-carbonyl)phenyl)-3-(4-methylpiperazin-1-yl)-5-(trifluoromethyl)benzamide,
(S)-1-(4-chloro-3-(trifluoromethyl)phenyl)-3-(4-(1-(2-((2-hydroxypropyl)amino)pyrimidin-4-yl)-1H-imidazole-2-carbonyl)phenyl)urea, and
(S)-1-(3,4-dichlorophenyl)-3-(4-(1-(2-((2-hydroxypropyl)amino)pyrimidin-4-yl)-1H-imidazole-2-carbonyl)phenyl)urea.

According to one embodiment of the present invention, when $Q_1$ is methylene (—$CH_2$— in Chemical Formula 1, the compound of Chemical Formula 1 may be prepared according to the following Reaction Formula 1.

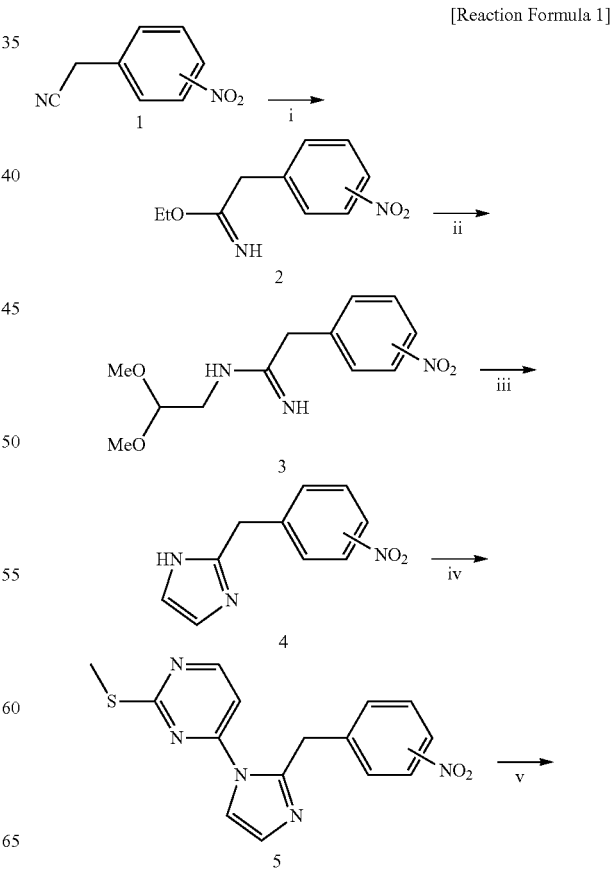

[Reaction Formula 1]

-continued

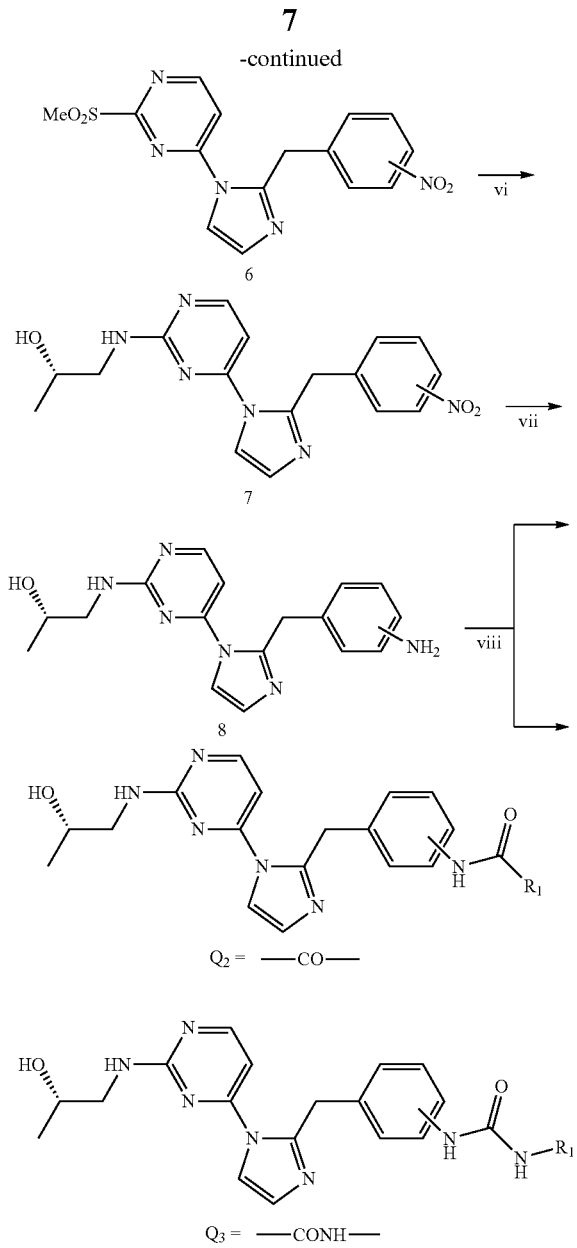

In Reaction Formula 1, the solvents and the reactants used and the reaction conditions such as temperature in the reaction steps (i) to (viii) may be exemplified as follows, but the present invention is not limited to or by them.

Step (i): HCl(g), EtOH, MC(CH$_2$Cl, methylene chloride), −10° C.
Step (ii): 2,2-dimethoxyethanamine, EtOH, 40° C.
Step (iii): 6N HCl in H$_2$O-MeOH, 90° C.
Step (iv): 4-chloro-2-(methylthio)pyrimidine, Pd(OAc)$_2$, BINAP, K$_3$PO$_4$, toluene, 130° C.
Step (v): 70% m-CPBA, MC, rt
Step (vi): (S)-1-aminopropan-2-ol, THF, 60° C.
Step (vii): Raney nickel, H$_2$, MeOH
Step (viii): R$_1$CO$_2$H, EDCI, TEA, HOBt, DMF or R$_1$NHCO$_2$H, THF, rt More specifically, in Reaction Formula 1, the synthesis of nitrobenzyl imidazole moiety (Compound 4) is started from 2-(4-nitrophenyl) acetonitrile (Compound 1). After forming ethyl 2-(4-nitrophenyl)acetimidate (Compound 2) by reacting Compound 1 with ethanol under dry hydrogen chloride gas, Compound 3 is formed by substituting Compound 2 with 2,2-dimethoxyethanamine and then nitrobenzyl imidazole (Compound 4) is formed through a strong acidic cyclization of the same.

4-chloro-2-(methylthio) pyrimidine is then introduced to Compound 4 in a modified Buchwald condition, and methylthio group thereof is oxidized into methyl sulfoxide (Compound 6) by using mCPBA. Methyl sulfoxide group is substituted with (S)-1-aminopropan-2-ol (Compound 7).

A nitro group on a benzyl ring is then reduced into amine (Compound 8), amide compound derivatives (when Q$_2$ is —CO—) can be obtained by coupled with various aromatic acids under EDCI(1-ethyl-3-(3-dimethylaminopropyl)carbodiimide)/HOBt(Hydroxybenzotriazole) condition, or urea compound derivatives (when Q$_2$ is —CONH—) can be obtained by directly coupled with aromatic isocyanate.

However, the preparation method of the compound of Chemical Formula 1 is not limited to above method, and it may be adequately modified by the method commonly applied to the technical field to which the present invention pertains with necessity.

According to another embodiment of the present invention, when Q$_1$ is —CO—, the compound of Chemical Formula 1 may be prepared according to the following Reaction Formula 2.

[Reaction Formula 2]

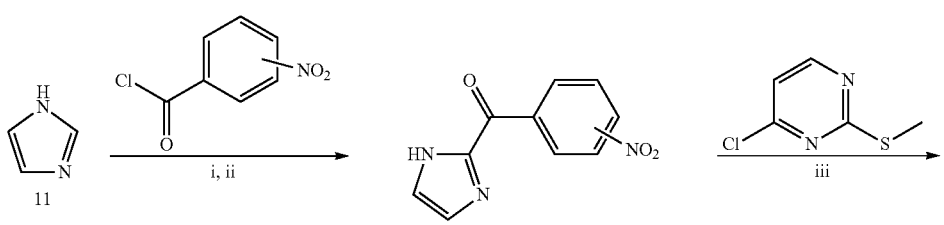

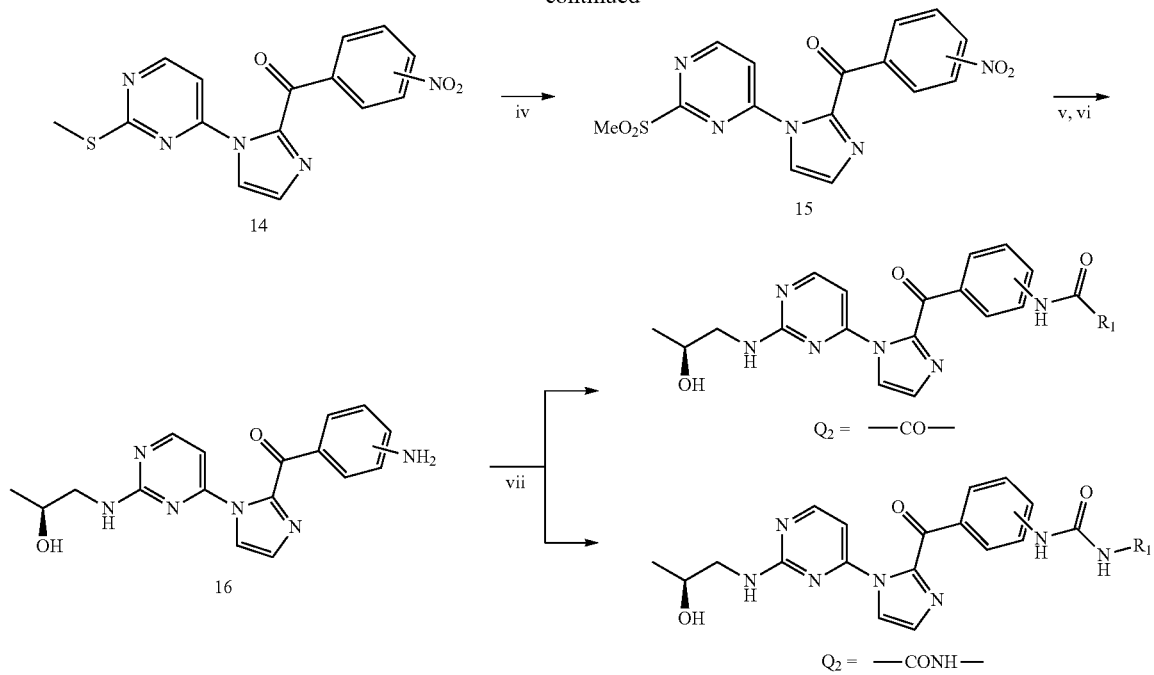

In Reaction Formula 2, the solvents and the reactants used and the reaction conditions such as temperature in the reaction steps (i) to (vii) may be exemplified as follows, but the present invention is not limited to or by them.

Step (i): pyridine, TEA, 0° C.→RT
Step (ii): 10 N NaOH
Step (iii): 4-chloro-2-(methylthio) pyrimidine, NaH, DMF 100° C.
Step (iv): 70% mCPBA, MC, rt
Step (v): (S)-1-aminopropan-2-ol, THF, 60° C.
Step (vi): Fe, HCl, EtOH.$H_2O$
Step (vii): $R_1CO_2H$, HATU, TEA, DMF or $R_1NHCO_2H$, THF More specifically, in Reaction Formula 2, imidazole (Compound 11) is directly coupled with 3-nitro benzoyl chloride or 4-nitro benzoyl chloride and then rearranged in a basic condition. The introduction of pyrimidyl moiety and the rest compounds may be carried out according to the method similar to Reaction Formula 1.

As disclosed above, the compound of Chemical Formula 1 of the present invention is increased in the flexibility of the molecular structure due to methylene group or carbonyl group positioned between pyrimidine and imidazole, and has a structural characteristic of that the tail moiety of the derivative compound can more easily approach to the secondary hydrophobic pocket. Accordingly, it is revealed that the derivative compound shows selective inhibition activity to various kinases and can be used to the pharmaceutic composition for preventing or treating cancer.

According to another aspect of the present invention, a pharmaceutic composition for preventing or treating cancer comprising the imidazole-1-yl pyrimidine derivative of Chemical Formula 1 or the pharmaceutically acceptable salt thereof as an active ingredient is provided.

The imidazole-1-yl pyrimidine derivative of Chemical Formula 1 or the pharmaceutically acceptable salt thereof shows the inhibition activity selectively to various protein kinases and can suppress the proliferation of abnormal cells.

For example, the imidazole-1-yl pyrimidine derivative of Chemical Formula 1 or the pharmaceutically acceptable salt thereof can show the proliferation inhibition activity to A375P human melanoma cell line or U937 human leukemic monocyte lymphoma cell line.

More preferably, the imidazole-1-yl pyrimidine derivative of Chemical Formula 1 or the pharmaceutically acceptable salt thereof shows selective and high inhibition activity to one or more of BRAF, BRAF mutants (for example, BRAF V599E, BRAF V600E and so on), or CRAF. Therefore, the pharmaceutic composition including the imidazole-1-yl pyrimidine derivative of Chemical Formula 1 or the pharmaceutically acceptable salt thereof as an active ingredient can be used as a selective inhibitor against BRAF, BRAF mutants, or CRAF for preventing or treating cancer related to the kinases. For example, the cancer may be melanoma or leukemia but the present invention is not limited to or by this.

The pharmaceutic composition according to the present invention including the imidazole-1-yl pyrimidine derivative of Chemical Formula 1 or the pharmaceutically acceptable salt thereof as an active ingredient may be formulated in the form of oral administration or parenteral administration according to standard pharmaceutical implementation. These formulations may include additives such as pharmaceutically acceptable carriers, adjurvants, diluent, and so on in addition to the active ingredient. When it is made into a medicine, additives such as a filler, an extender, a binder, a wetting agent, a disintegrating agent, a surfactant, and the like which are commonly used may be used, or an excipient.

Solid formulation for oral administration may include a tablet, a pill, powders, granules, a capsule, a troche, and so on. Such solid formulation may be prepared by mixing at least one excipient, for example, starch, calcium carbonate, sucrose, lactose, or gelatin, with the compound of Chemical Formula 1 according to the present invention or the pharmaceutically acceptable salt, the hydrate, or the solvate thereof.

Liquid formulation for oral administration may be a suspension, a solution, an emulsion, a syrup, and so on, and it may include various excipients, for example, a wetting agent, a sweeting agent, a flavoring agent, a preserving agent, and so on in addition to water and liquid paraffin which are diluents commonly used.

The formulation for parenteral administration may include a sterilized aqueous solution, a non-aqueous solvent, an emulsion, a lyophiled formulation, or a suppository. As the non-aqueous solvent and the emulsion, propyleneglycol, polyethleneglycol, vegetable oil such as olive oil, and injectable ester such as ethyloleate may be used.

Preferable dose of the compound of Chemical Formula 1 or the pharmaceutically acceptable salt thereof according to the present invention may be different according to the condition and the weight of patient, the severity of disease, the formation of drug, the administration route, and the term, but it can be properly selected by the method generally applied to the technical field to which the present invention pertains. Furthermore, the pharmaceutical composition according to the present invention may be administered to mammals including mouse, rat, domestic animals, and human through various routes. Every administration methods may be considered, and, for example, an oral administration, a rectal administration, or an intravenous, an intramuscular, a hypodermic, a cervical or an intracerbroventricular injection is possible.

Furthermore, the compound of Chemical Formula 1 or the pharmaceutically acceptable salt thereof according to the present invention has an activity with itself, but the possibility of that special internal environments or products of the metabolic process exhibit a medical action as effecters after it is absorbed into the body cannot be excluded.

Hereinafter, the present invention is explained in more detail through the following examples. However, the following examples are only for illustrating the present invention, and the scope of the present invention is not limited to or by them.

EXAMPLES

Example 1

Preparation of (S)—N-(3-((1-(2-(2-hydroxypropyl)amino)pyrimidin-4-yl)-1H-imidazol-2-yl)methyl)phenyl)-3-(4-methylpiperazin-1-yl)-5-(trifluoromethyl)benzamide Step 1: Preparation of ethyl 2-(3-nitrophenyl)acetimidate

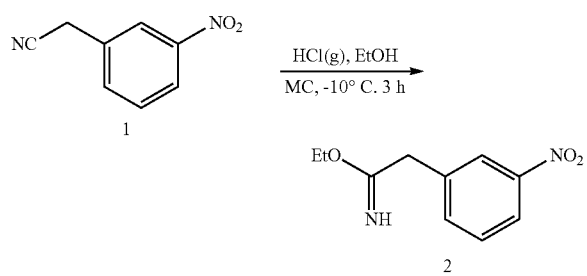

Compound 1 (1.2 g, 7.4 mmol) was added in EtOH (24 mL) and cooled to −78° C. At this time, MC (methylene chloride) was used as a cosolvent for maintaining the reacting solution uniformly. After the temperature was maintained to −78° C., HCl (g) was flowed for 20 mins. The reacting solution was stirred for 2 hrs below −10° C. for maintaining the reaction speed. After the reaction terminated, a product Compound 2 (1.5 g) was obtained by eliminating the solvent under reduced pressure and washing the residue 3 times with diethyl ether.

Step 2: Preparation of N-(2,2-dimethoxyethyl)-2-(3-nitrophenyl)acetimidamide

After dissolving Compound 2 (1.5 g, 7.72 mmol) in EtOH (70 ml), 2,2-dimethoxy ethanamine (1.05 g, 10.04 mmol) was slowly added therein and the solution was stirred for 4 hrs at 40° C. After the reaction terminated, a product Compound 3 was obtained by reducing the temperature to room temperature and carrying out a vacuum distillation.

Step 3: Preparation of 2-(3-nitrobenzyl)-1H-imidazole

After adding Compound 3 obtained in above Step in 6 N HCl aqueous solution (20 mL) and the solution was refluxed with stirring for about 1 hr at 90° C. After the reaction terminated, the solvent was eliminated under reduced pressure and pH of the solution was adjusted to 8 to 10 by slowly adding $K_2CO_3$ aqueous solution thereto. The product was extracted 3 times by using ethyl acetate, washed with water, dried by using anhydrous magnesium sulfate, and filtered. The filtered solution was distilled under reduced pressure and the concentrated residue was purified and separated by column chromatography (silica gel, methylene chloride: MeOH=10:1), and a product Compound 4 (630 mg, 41.9% for three steps yield) was obtained.

¹H NMR (400 MHz, DMSO-d₆) δ 8.12 (1H, s), 8.09 (1H, d, J=8.16), 7.71 (1H, d, J=7.50), 7.60 (1H, t, J=7.93), 7.03 (1H, s), 6.82 (1H, s)

Step 4: Preparation of 2-(methylthio)-4-(2-(3-nitrobenzyl)-1H-imidazol-1-yl)pyrimidine

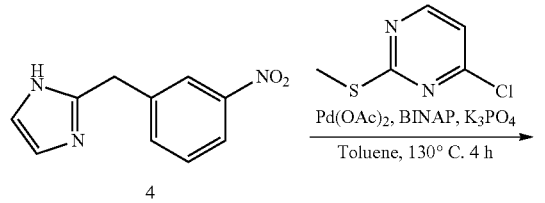

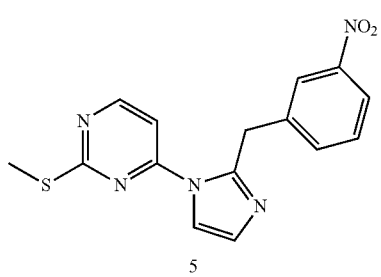

After dissolving Compound 4 (630 mg, 3.1 mmol) and all of 4-chloro-2-(methylthio)pyrimidine (497 mg, 3.1 mmol), Pd(OAC)₂ (69.5 mg, 0.31 mmol), BINAP (193 mg, 0.31 mmol), and K₃PO₄ (1.3 g, 6.2 mmol) in toluene (16 mL), the solution was refluxed with stirring for 4 hrs at 130° C. After the reaction terminated, the solution was cooled to room temperature and filtered with celite, and the filtered solution was concentrated by vacuum distillation. The residue was purified by column chromatography (silica gel, methylene chloride:MeOH=20:1), and a product Compound 5 (450 mg, 71.4%) was obtained.

¹H NMR (400 MHz, DMSO-d₆) δ 8.72 (1H, d, J=5.57), 8.06 (2H, m), 7.89 (1H, d, J=1.61), 7.63 (1H, d, J=7.62), 7.57 (1H, t, J=7.75), 7.47 (1H, d, J=5.59), 7.08 (1H, d, J=1.60), 4.64 (2H, s), 2.49 (3H, s)

Step 5: Preparation of 2-(methylsulfonyl)-4-(2-(3-nitrobenzyl)-1H-imidazol-1-yl)pyrimidine

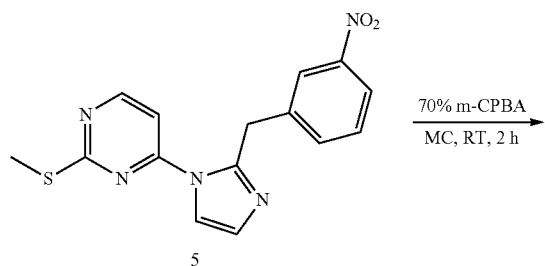

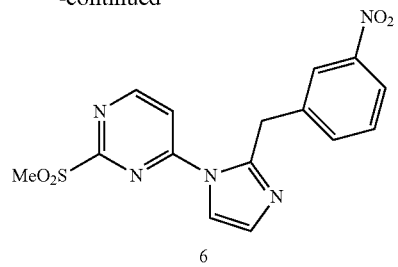

After dissolving Compound 5 (450 mg, 2.1 mmol) and 70% m-CPBA (1.08 g, 6.3 mmol) in MC (11 mL), the solution was stirred for about 2 hrs at room temperature. After the reaction terminated, the product was extracted with ethyl acetate and washed by using saturated NaHCO₃ aqueous solution. After the extracted organic layer was dried with magnesium sulfate anhydrous and filtered, the filtered solution was distilled under reduced pressure and the residue was purified by column chromatography (silica gel, ethyl acetate 100%), and a product Compound 6 (330 mg, 43.7%) was obtained.

¹H NMR (400 MHz, DMSO-d₆) δ9.16 (1H, d, J=5.68), 8.12-8.06 (3H, m), 8.17 (1H, d, J=1.71), 7.71 (1H, d, J=7.67), 7.56 (1H, t, J=7.87), 7.14 (1H, d, J=1.67), 4.72 (2H, s), 3.38 (3H, s)

Step 6: Preparation of (S)-1-(4-(2-(3-nitrobenzyl)-1H-imidazole-1-yl)pyrimidin-2-ylamino)propan-2-ol

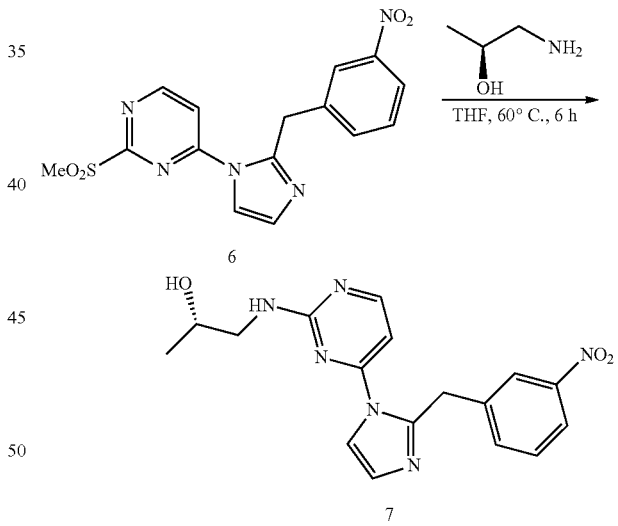

After dissolving Compound 6 (330 mg, 0.92 mmol) and (S)-1-aminopropan-2-ol (103.5 mg, 1.38 mmol) in THF (5 mL), the solution was stirred for 6 hrs at 60° C. After the reaction terminated, the solution was cooled to room temperature and distilled under reduced pressure. The concentrated residue was purified by column chromatography (silica gel, ethylene chloride:MeOH=10:1), and a product Compound 7 (310 mg, 95.1%) was obtained.

¹H NMR (400 MHz, CDCl₃) δ 8.30 (1H, d, J=5.41), 8.21 (1H, s), 8.06 (1H, d, J=8.11), 7.56 (1H, d, J=7.52), 7.44 (1H, t, J=7.90), 7.30 (1H, d, J=1.43), 7.11 (1H, d, J=1.56), 6.70 (1H, d, J=5.41), 4.60 (2H, s), 4.01 (1H, m), 3.52 (1H, m), 3.32 (1H, m), 1.21 (3H, d, J=6.10)

Step 7: Preparation of (S)-1-{4-[2-(3-aminobenzyl)-1H-imidazol-1-yl]pyrimidin-2-ylamino}-propan-2-ol

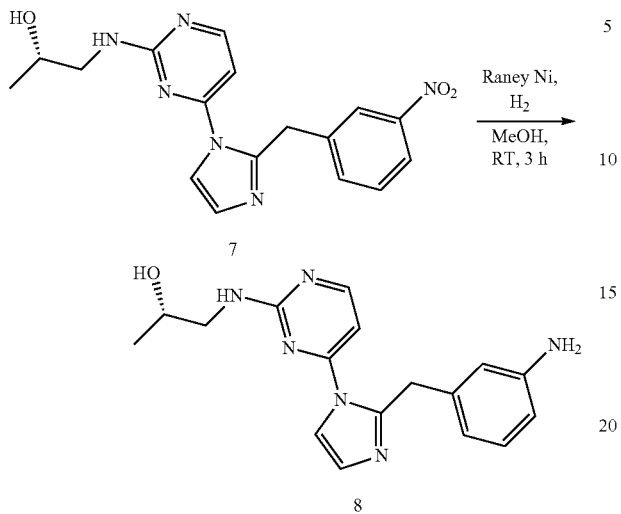

After dissolving Compound 7 (330 mg, 0.87 mmol) in MeOH (3 mL), Raney nickel was added therein and the solution was stirred for 3 hrs at room temperature under hydrogen gas. After the reaction terminated, the product was filtered with celite and the filtered solution was distilled under reduced pressure. The residue was purified by column chromatography (silica gel, methylene chloride:MeOH=10: 1), and a product Compound 8 (270 mg, 97%) was obtained.

$^1$H NMR (400 MHz, CDCl$_3$) δ 8.25 (1H, d, J=5.40), 7.33 (1H, d, J=1.28), 7.09 (1H, d, J=1.28), 7.02 (1H, t, J=7.89), 6.52-6.49 (3H, m), 6.46 (1H, d, J=5.38), 4.38 (2H, s), 3.97 (1H, m), 3.49 (1H, m), 3.25 (1H, m), 1.21 (3H, d, J=6.07)

Step 8: Preparation of (S)—N-(3-((1-(2-((2-hydroxypropyl)amino)pyrimidin-4-yl)-1H-imidazol-2-yl)methyl)phenyl)-3-(4-methylpiperazin-1-yl)-5-(trifluoromethyl)benzamide

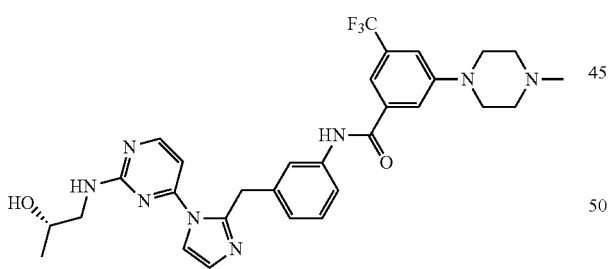

After dissolving (S)-1-((4-(2-(3-aminobenzyl)-1H-imidazol-1-yl)pyrimidin-2-yl)-amino)propan-2-ol (10 mg, 0.031 mmol) prepared in Step 7, 3-(4-methylpiperazin-1-yl)-5-(trifluoromethyl)benzoic acid (8.9 mg, 0.031 mmol), EDCI (8.9 mg, 0.047 mmol), HOBt (6.28 mg, 0.047 mmol), and TEA (6.27 mg, 0.062 mmol) in DMF (0.4 mL), the solution was stirred for about 5 hrs at 50° C. After the reaction terminated, ethyl acetate was added thereto and the product was washed with saturated NaHCO$_3$ aqueous solution. After the organic layer was dried with magnesium sulfate anhydrous and filtered, the solvent was eliminated under reduced pressure. The residue was purified by column chromatography (silica gel, methylene chloride:MeOH=10:1), and a product Compound 9a of (S)—N-(3-((1-(2-((2-hydroxypropyl)amino)pyrimidin-4-yl)-1H-imidazol-2-yl)methyl)phenyl)-3-(4-methylpiperazin-1-yl)-5-(trifluoromethyl)benzamide (9.1 mg, 49%) was obtained.

$^1$H NMR (400 MHz, DMSO-d$_6$) δ 10.28 (1H, s), 8.32 (1H, d, J=5.6 Hz), 7.68 (1H, s), 7.59-7.52 (3H, m), 7.38 (1H, s), 7.32 (1H, t, J=5.8 Hz), 7.20 (1H, t, J=7.8 Hz), 6.75 (1H, d, J=4 Hz), 4.73 (1H, br), 4.55 (2H, s), 3.76 (2H, br), 3.23 (4H, m), 3.15 (1H, br), 2.65 (4H, m), 2.36 (3H, s), 1.23 (3H, d, J=8.13 Hz)

Example 2

Preparation of (S)—N-(3-((1-(2-((2-hydroxypropyl)amino)pyrimidin-4-yl)-1H-imidazol-2-yl)methyl)phenyl)-3,5-dimethylbenzamide

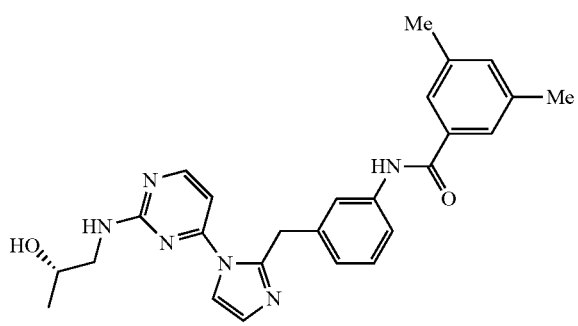 [SMILES: Cc1cc(C)cc(C(=O)Nc2cccc(Cc3nccn3-c3ccnc(NC[C@H](C)O)n3)c2)c1]

Steps 1 to 7 of Example 1 were carried out in the same manner. In the next step, (S)—N-(3-((1-(2-((2-hydroxypropyl)amino)pyrimidin-4-yl)-1H-imidazol-2-yl)methyl)phenyl)-3,5-dimethylbenzamide (Compound 9b), a product compound, was obtained according to the same reaction as in Example 1, except that 3,5-dimethylbenzoic acid (0.031 mmol) was used instead of 3-(4-methylpiperazin-1-yl)-5-(trifluoromethyl)benzoic acid.

$^1$H NMR (400 MHz, CDCl$_3$) δ 8.40-8.33 (2H, m), 7.48 (2H, s), 7.32-7.26 (2H, m), 7.20-7.15 (5H, m), 6.45 (1H, d, J=5.2 Hz), 4.65 (2H, s), 4.03 (1H, m), 3.58 (1H, m), 3.35 (1H, m), 2.36 (6H, s), 1.19 (3H, d, J=6.4 Hz), Yield=56%

Example 3

Preparation of (S)—N-(4-((1-(2-((2-hydroxypropyl)amino)pyrimidin-4-yl)-1H-imidazol-2-yl)methyl)phenyl) pyrazine-2-carboxamide

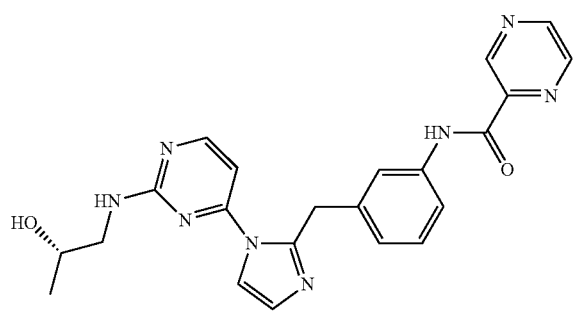 [SMILES: C[C@H](O)CNc1nccc(-n2ccnc2Cc2cccc(NC(=O)c3cnccn3)c2)n1]

Steps 1 to 7 of Example 1 were carried out in the same manner. In the next step, (S)—N-(4-((1-(2-((2-hydroxypropyl)amino)pyrimidin-4-yl)-1H-imidazol-2-yl)methyl)phenyl)pyrazine-2-carboxamide (Compound 9c), a product compound, was obtained according to the same reaction as in Example 1, except that pyrazine-2-carboxylic acid (0.031 mmol) was used instead of 3-(4-methylpiperazin-1-yl)-5-(trifluoromethyl)benzoic acid.

¹H NMR (400 MHz, DMSO-d₆) δ 10.61 (1H, s), 9.27 (1H, d, J=1.2 Hz), 8.92 (1H, d, J=2.4 Hz), 8.79 (1H, m), 8.32 (1H, d, J=5.2 Hz), 7.70 (3H, m), 7.32 (1H, t, J=5.4 Hz), 7.21 (1H, t, J=7.6 Hz), 7.01 (1H, d, J=1.2 Hz), 6.72 (1H, d, J=4.4 Hz), 4.69 (1H, br), 4.54 (2H, s) 3.77 (1H, br), 3.15 (2H, br) 1.01 (3H, br), Yield=77%

Example 4

Preparation of (S)-2-(2-fluorophenyl)-N-(3-((1-(2-((2-hydroxypropyl)amino)pyrimidin-4-yl)-1H-imidazol-2-yl)methyl)phenyl)acetamide

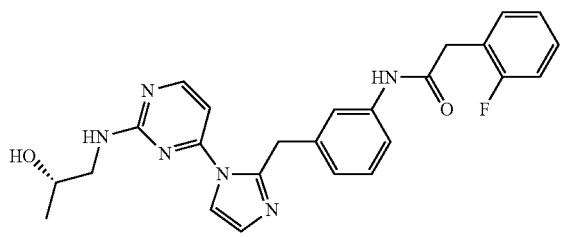 [SMILES: C[C@H](O)CNc1nccc(-n2ccnc2Cc2cccc(NC(=O)Cc3ccccc3F)c2)n1]

Steps 1 to 7 of Example 1 were carried out in the same manner. In the next step, (S)-2-(2-fluorophenyl)-N-(3-((1-(2-((2-hydroxypropyl)amino)pyrimidin-4-yl)-1H-imidazol-2-yl) methyl)phenyl)acetamide (Compound 9d), a product compound, was obtained according to the same reaction as in Example 1, except that (2-fluorophenyl)acetic acid (0.031 mmol) was used instead of 3-(4-methylpiperazin-1-yl)-5-(trifluoromethyl)benzoic acid.

¹H NMR (400 MHz, CDCl₃) δ 8.52 (1H, s), 8.32 (1H, d, J=5.2 Hz), 7.33 (1H, t, J=7.6 Hz), 7.28-7.25 (3H, m), 7.19 (1H, s), 7.13-7.03 (5H, m), 6.42 (1H, d, J=5.2 Hz), 4.50 (2H, s), 4.00-3.93 (1H, m), 3.78 (2H, s), 3.53 (1H, br), 3.29-3.22 (1H, m), 1.17 (3H, d, J=6.4 Hz), Yield=77%

Example 5

Preparation of (S)—N-(3-((1-(2-((2-hydroxypropyl) amino)pyrimidin-4-yl)-1H-imidazol-2-yl)methyl) phenyl)-1-phenyl-5-(trifluoromethyl)-1H-pyrazole-4-carboxamide

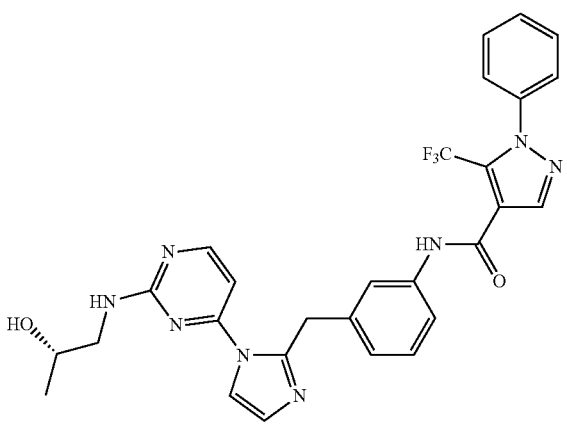 [SMILES: C[C@H](O)CNc1nccc(-n2ccnc2Cc2cccc(NC(=O)c3cnn(-c4ccccc4)c3C(F)(F)F)c2)n1]

Steps 1 to 7 of Example 1 were carried out in the same manner. In the next step, (S)—N-(3-((1-(2-((2-hydroxypropyl)amino)pyrimidin-4-yl)-1H-imidazol-2-yl)methyl)phenyl)-1-phenyl-5-(trifluoromethyl)-1H-pyrazole-4-carboxamide (Compound 9e), a product compound, was obtained according to the same reaction as in Example 1, except that 1-phenyl-5-(trifluoromethyl)-1H-pyrazole-4-carboxylic acid (0.031 mmol) was used instead of 3-(4-methylpiperazin-1-yl)-5-(trifluoromethyl)benzoic acid.

¹H NMR (400 MHz, CDCl₃) δ 9.17 (1H, s), 8.21-8.15 (2H, m), 8.10 (1H, d, J=7.91 Hz), 7.77-7.69 (4H, m), 7.53-7.50 (2H, m), 7.33 (1H, t, J=7.88 Hz), 7.16 (1H, d, J=1.38 Hz), 7.13 (1H, d, J=5.58 Hz), 6.26-6.24 (1H, br), 5.85-5.84 (1H, br), 4.51 (2H, s), 3.48-3.46 (1H, m), 3.20-3.13 (2H, m), 1.24 (3H, d, J=3.22 Hz), Yield=80%

Example 6

Preparation of (S)-4-chloro-N-(3-((1-(2-((2-hydroxypropyl)amino)pyrimidin-4-yl)-1H-imidazol-2-yl)methyl) phenyl)benzamide

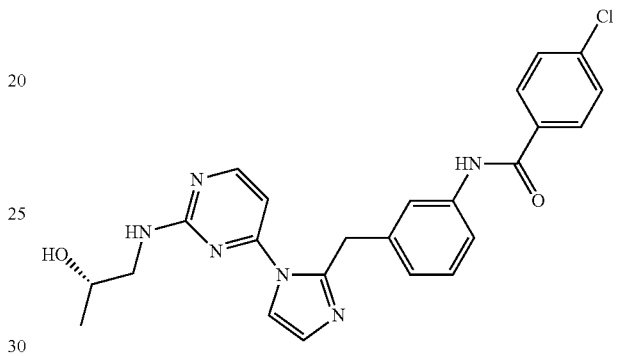

Steps 1 to 7 of Example 1 were carried out in the same manner. In the next step, (S)-4-chloro-N-(3-((1-(2-((2-hydroxypropyl)amino)pyrimidin-4-yl)-1H-imidazol-2-yl) methyl)phenyl)benzamide (Compound 9f), a product compound, was obtained according to the same reaction as in Example 1, except that 4-chlorobenzoic acid (0.031 mmol) was used instead of 3-(4-methylpiperazin-1-yl)-5-(trifluoromethyl)benzoic acid.

¹H NMR (400 MHz, CDCl₃) δ 8.48 (1H, s), 8.30 (1H, d, J=5.2 Hz), 7.85 (2H, d, J=8.4 Hz), 7.44 (2H, d, J=8.0 Hz), 7.28-7.26 (3H, m), 7.21-7.14 (2H, m), 6.99 (1H, s), 6.46 (1H, d, J=4.8 Hz), 4.52 (2H, s), 4.02 (1H, m), 3.60 (1H, m), 3.34 (1H, m), 1.20 (3H, d, J=6.4 Hz), Yield=87%

Example 7

Preparation of (S)—N-(3-((1-(2-((2-hydroxypropyl) amino)pyrimidin-4-yl)-1H-imidazol-2-yl)methyl) phenyl) quinoline-2-carboxamide

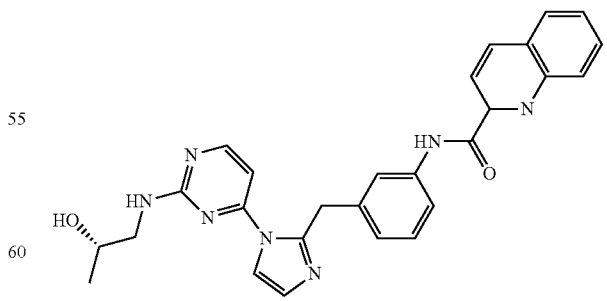

Steps 1 to 7 of Example 1 were carried out in the same manner. In the next step, (S)—N-(3-((1-(2-((2-hydroxypropyl)amino)pyrimidin-4-yl)-1H-imidazol-2-yl)methyl)phenyl)quinoline-2-carboxamide (Compound 9g), a product compound, was obtained according to the same reaction as in Example 1, except that quinoline-2-carboxylic acid (0.031 mmol) was used instead of 3-(4-methylpiperazin-1-yl)-5-(trifluoromethyl)benzoic acid.

$^1$H NMR (400 MHz, DMSO) δ 10.55 (1H, s), 9.32 (1H, d, J=2.4 Hz), 8.92 (1H, d, J=2 Hz), 8.35 (1H, d, J=5.2 Hz), 8.14-8.10 (2H, m), 7.89 (1H, t, J=4.8 Hz), 7.76-7.72 (2H, m), 7.70-7.63 (2H, m), 7.38 (1H, t, J=5.8 Hz), 7.24 (1H, t, J=7.4 Hz), 7.211 (1H, s), 6.75 (1H, d, J=4 Hz), 4.73 (1H, br), 4.58 (1H, s), 3.77 (1H, br), 3.16 (1H, br), 1.22 (3H, s), Yield=74%

Example 8

Preparation of (S)—N-(3-((1-(2-((2-hydroxypropyl)amino)pyrimidin-4-yl)-1H-imidazol-2-yl)methyl)phenyl)-1H-indole-3-carboxamide

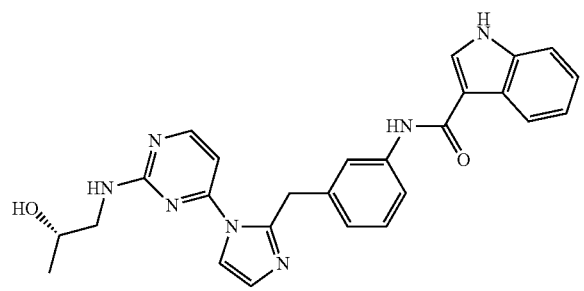 [SMILES: C[C@H](O)CNc1nccc(-n2ccnc2Cc2cccc(NC(=O)c3c[nH]c4ccccc34)c2)n1]

Steps 1 to 7 of Example 1 were carried out in the same manner. In the next step, (S)—N-(3-((1-(2-((2-hydroxypropyl)amino)pyrimidin-4-yl)-1H-imidazol-2-yl)methyl)phenyl)-1H-indole-3-carboxamide (Compound 9h), a product compound, was obtained according to the same reaction as in Example 1, except that 1H-indole-3-carboxylic acid (0.031 mmol) was used instead of 3-(4-methylpiperazin-1-yl)-5-(trifluoromethyl)benzoic acid.

$^1$H NMR (400 MHz, DMSO-$d_6$) δ 10.89 (1H, s), 10.09 (1H, s), 8.43 (1H, d, J=5.2 Hz), 8.04 (1H, s), 7.57 (1H, d, J=8.0 Hz), 7.52-7.42 (3H, m), 7.34 (1H, d, J=8.0 Hz), 7.23 (1H, s), 7.17 (1H, t, J=8.0 Hz), 7.06 (1H, t, J=7.4 Hz), 6.95 (1H, t, J=7.4 Hz), 6.83-6.78 (2H, m), 4.61 (2H, s), 3.78 (1H, br), 3.69 (2H, s), 3.30 (1H, m), 3.09 (1H, m), 1.01 (3H, s), Yield=75%

Example 9

Preparation of (S)—N-(3-((1-(2-((2-hydroxypropyl)amino)pyrimidin-4-yl)-1H-imidazol-2-yl)methyl)phenyl)-1H-benzo[d][1,2,3]triazole-5-carboxamide

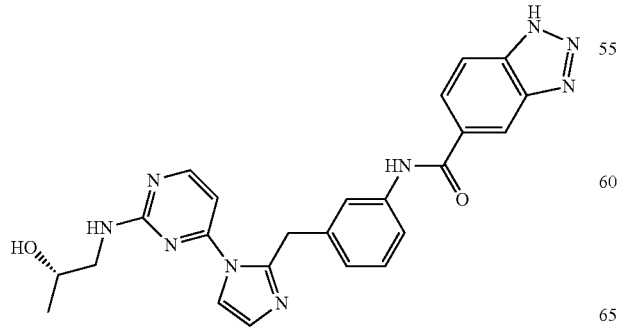

Steps 1 to 7 of Example 1 were carried out in the same manner. In the next step, (S)—N-(3-((1-(2-((2-hydroxypropyl)amino)pyrimidin-4-yl)-1H-imidazol-2-yl)methyl)phenyl)-1H-benzo[d][1,2,3]triazole-5-carboxamide (Compound 9i), a product compound, was obtained according to the same reaction as in Example 1, except that 1H-benzotriazole-5-carboxylic acid (0.031 mmol) was used instead of 3-(4-methylpiperazin-1-yl)-5-(trifluoromethyl)benzoic acid.

$^1$H NMR (400 MHz, DMSO-$d_6$) δ 10.38 (1H, s), 8.38 (1H, d, J=5.2 Hz), 7.98 (1H, d, J=8.4 Hz), 7.86 (1H, s), 7.62-7.52 (3H, m), 7.42 (1H, d, J=7.6 Hz), 7.28 (2H, m), 6.83-6.78 (2H, m), 4.73 (1H, br), 4.61 (1H, s), 3.76 (1H, br), 3.19 (2H, m), 1.23 (3H, s), Yield=47%

Example 10

Preparation of (S)—N-(3-((1-(2-((2-hydroxypropyl)amino)pyrimidin-4-yl)-1H-imidazol-2-yl)methyl)phenyl)isonicotinamide

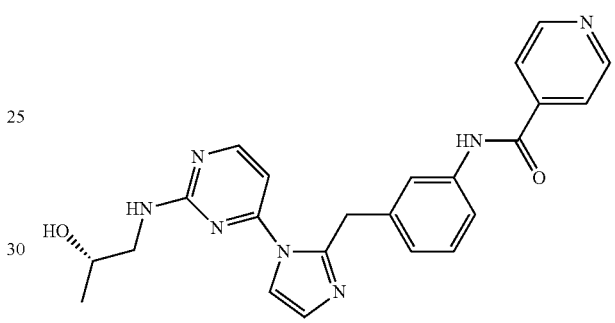

Steps 1 to 7 of Example 1 were carried out in the same manner. In the next step, (S)—N-(3-((1-(2-((2-hydroxypropyl)amino)pyrimidin-4-yl)-1H-imidazol-2-yl)methyl)phenyl)isonicotinamide (Compound 9j), a product compound, was obtained according to the same reaction as in Example 1, except that pyridine-4-carboxylic acid (0.031 mmol) was used instead of 3-(4-methylpiperazin-1-yl)-5-(trifluoromethyl)benzoic acid.

$^1$H NMR (400 MHz, DMSO-$d_6$) δ 10.41 (1H, s), 8.76 (2H, d, J=6 Hz), 8.32 (1H, d, J=5.2 Hz), 7.82 (2H, d, J=6 Hz), 7.69 (1H, s), 7.55 (2H, m), 7.30 (1H, t, J=6 Hz), 7.21 (1H, d, J=5.2 Hz), 4.69 (2H, s), 3.77 (1H, m), 3.21-3.16 (2H, m), 1.02 (3H, s), Yield=37%

Example 11

Preparation of (S)-2-([1,1'-biphenyl]-4-yl)-N-(3-((1-(2-((2-hydroxypropyl)amino)pyrimidin-4-yl)-1H-imidazol-2-yl)methyl)phenyl)acetamide

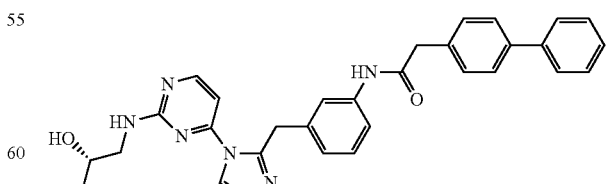

Steps 1 to 7 of Example 1 were carried out in the same manner. In the next step, (S)-2-([1,1'-biphenyl]-4-yl)-N-(3-((1-(2-((2-hydroxypropyl)amino)pyrimidin-4-yl)-1H-imidazol-2-yl)methyl)phenyl)acetamide (Compound 9k), a product compound, was obtained according to the same reaction as in Example 1, except that biphenyl-4-ylacetic acid (0.031 mmol) was used instead of 3-(4-methylpiperazin-1-yl)-5-(trifluoromethyl)benzoic acid.

$^1$H NMR (400 MHz, CDCl$_3$) δ 9.63 (1H, s), 8.31 (1H, d, J=4.8 Hz), 7.70 (1H, s), 7.52 (3H, m), 7.40 (4H, m), 7.33 (2H, m), 7.28 (3H, m), 6.94 (2H, m), 6.31 (1H, d, J=4.8 Hz), 4.47 (2H, s), 4.04 (1H, m), 3.82 (2H, s), 3.62 (1H, m), 3.32 (1H, m), 1.22 (3H, d, J=6.40 Hz), Yield=80%

Example 12

Preparation of (S)—N-(3-((1-(2-((2-hydroxypropyl) amino)pyrimidin-4-yl)-1H-imidazol-2-yl)methyl) phenyl)-[1,1'-biphenyl]-4-carboxamide

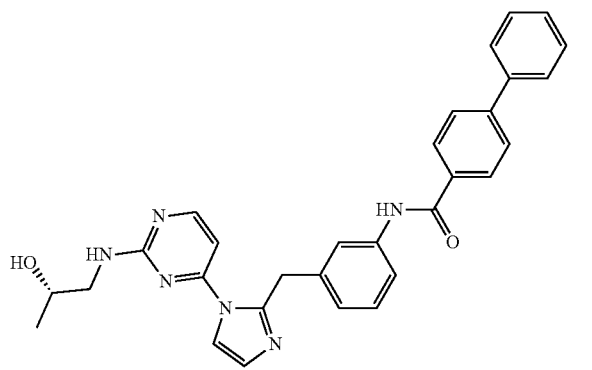 [SMILES: C[C@H](O)CNc1nccc(-n2ccnc2Cc2cccc(NC(=O)c3ccc(-c4ccccc4)cc3)c2)n1]

Steps 1 to 7 of Example 1 were carried out in the same manner. In the next step, (S)—N-(3-((1-(2-((2-hydroxypropyl)amino)pyrimidin-4-yl)-1H-imidazol-2-yl)methyl)phenyl)-[1,1'-biphenyl]-4-carboxamide (Compound 9l), a product compound, was obtained according to the same reaction as in Example 1, except that biphenyl-4-carboxylic acid (0.031 mmol) was used instead of 3-(4-methylpiperazin-1-yl)-5-(trifluoromethyl)benzoic acid.

$^1$H NMR (400 MHz, DMSO-d$_6$) δ 10.21 (1H, s), 8.32 (1H, d, J=5.2 Hz), 8.03 (2H, d, J=8.4 Hz), 7.82 (2H, d, J=8.4 Hz), 7.76-7.75 (2H, m), 7.69 (1H, s), 7.61-7.58 (2H, m), 7.53-7.49 (2H, m), 7.34 (1H, m), 7.32 (1H, t, J=5.8 Hz), 7.20 (1H, t, J=7.8 Hz), 7.01 (1H, d, J=1.2 Hz), 6.73 (1H, d, J=5.2 Hz), 4.69-4.54 (1H, m), 4.53 (2H, s), 3.77-3.58 (1H, br), 3.25-3.17 (1H, m), 1.02 (3H, s), Yield=83%

Example 13

Preparation of (S)—N-(3-((1-(2-((2-hydroxypropyl) amino)pyrimidin-4-yl)-1H-imidazol-2-yl)methyl) phenyl)-[1,1'-biphenyl]-2-carboxamide

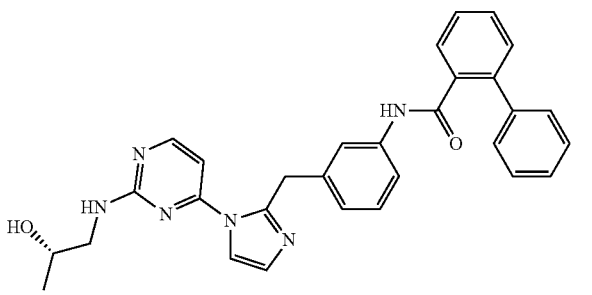 [SMILES: C[C@H](O)CNc1nccc(-n2ccnc2Cc2cccc(NC(=O)c3ccccc3-c3ccccc3)c2)n1]

Steps 1 to 7 of Example 1 were carried out in the same manner. In the next step, (S)—N-(3-((1-(2-((2-hydroxypropyl)amino)pyrimidin-4-yl)-1H-imidazol-2-yl)methyl)phenyl)-[1,1'-biphenyl]-2-carboxamide (Compound 9m), a product compound, was obtained according to the same reaction as in Example 1, except that biphenyl-2-carboxylic acid (0.031 mmol) was used instead of 3-(4-methylpiperazin-1-yl)-5-(trifluoromethyl)benzoic acid.

$^1$H NMR (400 MHz, DMSO-d$_6$) δ 10.37 (1H, s), 8.82 (1H, d, J=5.2 Hz), 7.68 (1H, s), 7.57-7.43 (2H, m), 7.41-7.34 (4H, m), 7.30-7.26 (2H, m), 7.09 (1H, d, J=5.2 Hz), 4.46 (1H, s), 3.75 (2H, s), 3.53 (1H, m), 3.22-3.13 (2H, m), 1.01 (3H, s), Yield=75%

Example 14

Preparation of (S)-1-acetyl-N-(3-((1-(2-((2-hydroxypropyl)amino)pyrimidin-4-yl)-1H-imidazol-2-yl) methyl)phenyl)piperidine-4-carboxamide

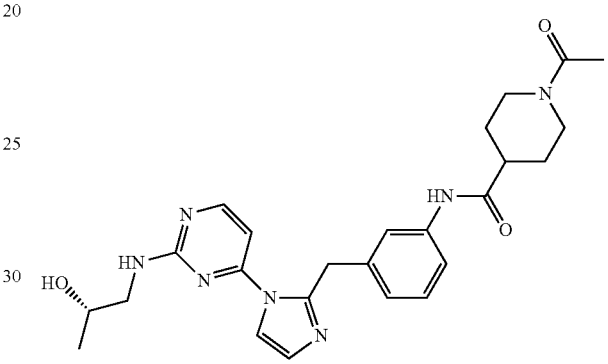

Steps 1 to 7 of Example 1 were carried out in the same manner. In the next step, (S)-1-acetyl-N-(3-((1-(2-((2-hydroxypropyl)amino)pyrimidin-4-yl)-1H-imidazol-2-yl) methyl)phenyl)piperidine-4-carboxamide (Compound 9n), a product compound, was obtained according to the same reaction as in Example 1, except that 1-acetylpiperidine-4-carboxylic acid (0.031 mmol) was used instead of 3-(4-methylpiperazin-1-yl)-5-(trifluoromethyl)benzoic acid.

$^1$H NMR (400 MHz, DMSO-d$_6$) δ 9.84 (1H, s), 8.31 (1H, d, J=5.6 Hz), 7.68 (1H, s), 7.43-7.39 (2H, m), 7.30 (1H, t, J=6 Hz), 7.12 (1H, t, J=7.8 Hz), 6.99 (1H, s), 6.69 (1H, d, J=4.8 Hz), 4.75 (1H, m), 4.47 (2H, s), 4.39-4.36 (1H, m), 3.86-3.83 (1H, m), 3.75 (1H, br), 3.25 (1H, m), 3.06-2.99 (1H, m), 2.58-2.54 (1H, m), 1.97 (3H, s), 1.93-1.78 (1H, m), 1.56-1.41 (4H, m), 1.23 (3H, s), Yield=61%

Example 15

Preparation of (S)-2-((2-cyanophenyl)thio)-N-(3-((1-(2-((2-hydroxypropyl)amino)pyrimidin-4-yl)-1H-imidazol-2-yl)methyl)phenyl)benzamide

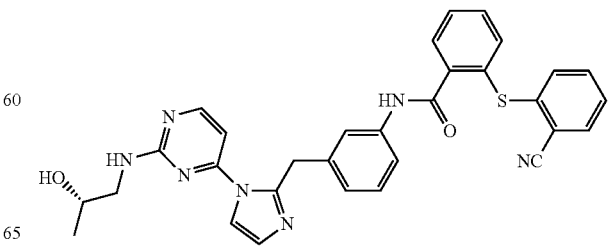

Steps 1 to 7 of Example 1 were carried out in the same manner. In the next step, (S)-2-((2-cyanophenyl)thio)-N-(3-((1-(2-((2-hydroxypropyl)amino)pyrimidin-4-yl)-1H-imidazol-2-yl)methyl)phenyl)benzamide (Compound 9o), a product compound, was obtained according to the same reaction as in Example 1, except that 2-[(2-cyanophenyl)sulfanyl]benzoic acid (0.031 mmol) was used instead of 3-(4-methylpiperazin-1-yl)-5-(trifluoromethyl)benzoic acid.

$^1$H NMR (400 MHz, DMSO-d$_6$) δ 10.43 (1H, s), 8.31 (1H, d, J=5.2 Hz), 7.91 (1H, d, J=7.6 Hz), 7.67-7.63 (3H, m), 7.35-7.02 (4H, m), 7.52-7.45 (5H, m), 7.39 (1H, d, J=8.0 Hz), 7.31 (1H, t, J=5.4 Hz), 7.19-7.14 (2H, m), 7.00 (1H, s), 6.71 (1H, d, J=5.6 Hz), 4.72 (1H, br), 4.51 (2H, s) 3.77 (1H, br), 3.20-3.10 (2H, br), 1.23 (3H, s), Yield=75%

Example 16

Preparation of (R)-6-hydroxy-N-(3-((1-(2-(((S)-2-hydroxypropyl)amino)pyrimidin-4-yl)-1H-imidazol-2-yl)methyl)phenyl)-2,5,7,8-tetramethylchromane-2-carboxamide

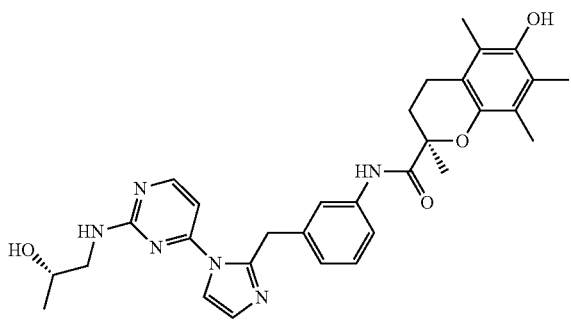 [SMILES: Cc1c(C)c2c(c(C)c1O)CC[C@](C)(C(=O)Nc1cccc(Cc3nccn3-c3ccnc(NC[C@H](C)O)n3)c1)O2]

Steps 1 to 7 of Example 1 were carried out in the same manner. In the next step, (R)-6-hydroxy-N-(3-((1-(2-(((S)-2-hydroxypropyl)amino)pyrimidin-4-yl)-1H-imidazol-2-yl)methyl)phenyl)-2,5,7,8-tetramethylchromane-2-carboxamide (Compound 9p), a product compound, was obtained according to the same reaction as in Example 1, except that (2S)-6-hydroxy-2,5,7,8-tetramethyl-3,4-dihydro-2H-chromene-2-carboxylic acid (0.031 mmol) was used instead of 3-(4-methylpiperazin-1-yl)-5-(trifluoromethyl)benzoic acid.

$^1$H NMR (400 MHz, DMSO-d$_6$) δ 9.04 (1H, s), 8.29 (1H, d, J=5.2 Hz), 7.67 (1H, s), 7.55 (1H, s), 7.42-7.30 (2H, m), 7.11 (1H, t, J=7.8 Hz), 6.68 (1H, d, J=5.6 Hz), 4.74 (1H, br), 4.47 (2H, s) 3.78 (1H, br), 3.25-3.10 (2H, br), 2.59-2.53 (1H, m), 2.33-2.26 (1H, m), 2.14 (3H, s), 2.07 (3H, s), 1.98 (3H, s), 1.96-1.93 (1H, m), 1.81-1.74 (1H, m) 1.47 (3H, s), Yield=65%

Example 17

Preparation of (S)-2,2-bis(4-chlorophenyl)-N-(3-((1-(2-(2-hydroxypropylamino)pyrimidin-4-yl)-1H-imidazol-2-yl)methyl)phenyl)acetamide

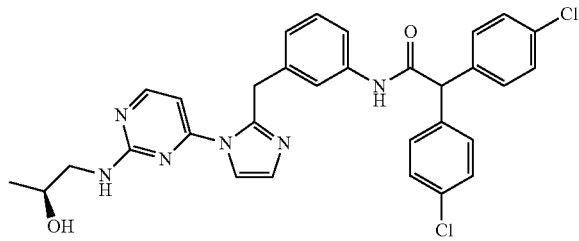 [SMILES: C[C@H](O)CNc1nccc(-n2ccnc2Cc2cccc(NC(=O)C(c3ccc(Cl)cc3)c3ccc(Cl)cc3)c2)n1]

Steps 1 to 7 of Example 1 were carried out in the same manner. In the next step, (S)-2,2-bis(4-chlorophenyl)-N-(3-((1-(2-(2-hydroxypropylamino)pyrimidin-4-yl)-1H-imidazol-2-yl)methyl)phenyl)acetamide (Compound 9q), a product compound, was obtained according to the same reaction as in Example 1, except that bis(4-chlorophenyl)acetic acid (0.031 mmol) was used instead of 3-(4-methylpiperazin-1-yl)-5-(trifluoromethyl)benzoic acid.

$^1$H NMR (400 MHz, DMSO-d$_6$) δ 10.38 (1H, s), 8.30 (1H, d, J=5.6 Hz), 7.66 (1H, s), 7.41-7.39 (6H, m), 7.33-7.31 (6H, m), 7.14 (1H, t, J=7.6 Hz), 6.99 (1H, s), 6.68 (1H, d, J=5.6 Hz), 5.13 (2H, s), 4.74 (1H, br), 4.47 (2H, s) 3.78 (1H, br), 3.25-3.10 (2H, br), 1.03 (1H, s), Yield=69%

Example 18

Preparation of (S)—N-(3-((1-(2-((2-hydroxypropyl)amino)pyrimidin-4-yl)-1H-imidazol-2-yl)methyl)phenyl)-3-morpholino-2-(trifluoromethyl)benzamide

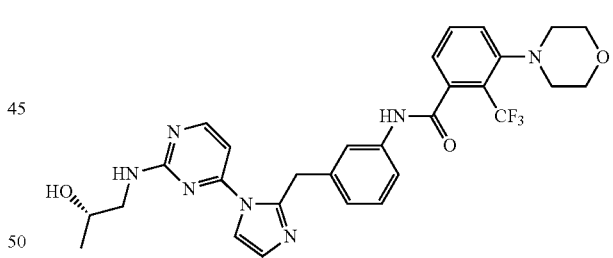

Steps 1 to 7 of Example 1 were carried out in the same manner. In the next step, (S)—N-(3-((1-(2-((2-hydroxypropyl)amino)pyrimidin-4-yl)-1H-imidazol-2-yl)methyl)phenyl)-3-morpholino-2-(trifluoromethyl)benzamide (Compound 9r), a product compound, was obtained according to the same reaction as in Example 1, except that 3-(morpholin-4-yl)-2-(trifluoromethyl)benzoic acid (0.031 mmol) was used instead of 3-(4-methylpiperazin-1-yl)-5-(trifluoromethyl)benzoic acid.

$^1$H NMR (400 MHz, DMSO-d$_6$) δ 10.32 (1H, s), 8.38 (1H, d, J=5.2 Hz), 8.21-8.19 (2H, m), 7.84 (1H, s), 7.65-7.58 (3H, m), 7.43 (1H, t, J=7.2 Hz), 7.21-7.23 (2H, m), 6.78 (1H, d, J=5.2 Hz), 4.59 (2H, s), 3.80 (1H, m), 3.78 (4H, t, J=4.4 Hz), 3.13 (1H, m), 2.95 (4H, t, J=4.6 Hz), 1.23 (3H, s), Yield=48%

Example 19

Preparation of (S)-4-chloro-N-(3-((1-(2-((2-hydroxypropyl)amino)pyrimidin-4-yl)-1H-imidazol-2-yl)methyl)phenyl)-3-(trifluoromethyl)benzamide

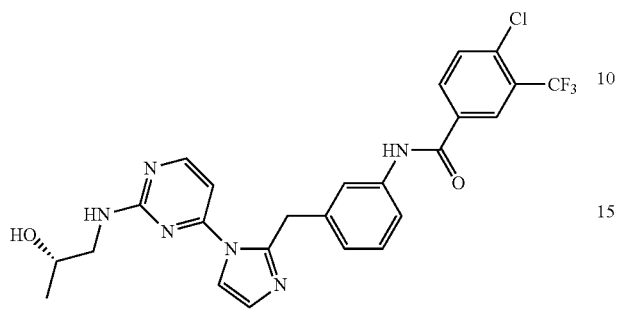

Steps 1 to 7 of Example 1 were carried out in the same manner. In the next step, (S)-4-chloro-N-(3-((1-(2-((2-hydroxypropyl)amino)pyrimidin-4-yl)-1H-imidazol-2-yl)methyl)phenyl)-3-(trifluoromethyl)benzamide (Compound 9s), a product compound, was obtained according to the same reaction as in Example 1, except that 4-chloro-3-(trifluoromethyl)benzoic acid (0.031 mmol) was used instead of 3-(4-methylpiperazin-1-yl)-5-(trifluoromethyl)benzoic acid.

$^1$H NMR (400 MHz, CDCl$_3$) δ 8.98 (1H, s), 8.32 (1H, d, J=5.2 Hz), 8.25 (1H, s), 8.10 (1H, d, J=11.2 Hz), 7.62 (1H, d, J=8.4 Hz), 7.31-7.29 (3H, m), 7.19-7.14 (2H, m), 6.96 (1H, s), 6.46 (1H, d, J=5.2 Hz), 4.49 (2H, s), 4.07 (1H, m), 3.59 (1H, m), 3.32 (1H, m), 1.20 (3H, d, J=6.4 Hz), Yield=57%

Example 20

Preparation of (S)—N-(3-((1-(2-((2-hydroxypropyl)amino)pyrimidin-4-yl)-1H-imidazol-2-yl)methyl)phenyl)-3-morpholino-5-(trifluoromethyl)benzamide

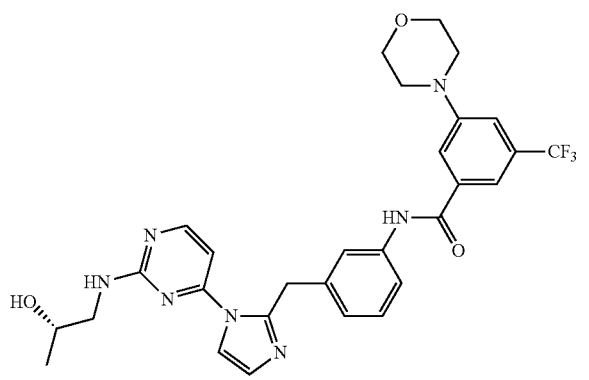 [SMILES: C[C@H](O)CNc1nccc(-n2ccnc2Cc2cccc(NC(=O)c3cc(N4CCOCC4)cc(C(F)(F)F)c3)c2)n1]

Steps 1 to 7 of Example 1 were carried out in the same manner. In the next step, (S)—N-(3-((1-(2-((2-hydroxypropyl)amino)pyrimidin-4-yl)-1H-imidazol-2-yl)methyl)phenyl)-3-morpholino-5-(trifluoromethyl)benzamide (Compound 9t), a product compound, was obtained according to the same reaction as in Example 1, except that 3-(morpholin-4-yl)-5-(trifluoromethyl)benzoic acid (0.031 mmol) was used instead of 3-(4-methylpiperazin-1-yl)-5-(trifluoromethyl)benzoic acid.

$^1$H NMR (400 MHz, CDCl$_3$) δ 8.65 (1H, s), 8.21 (1H, d, J=5.2 Hz), 7.67 (1H, s), 7.61 (1H, s), 7.28-7.20 (3H, m), 7.18-6.94 (4H, m), 6.46 (1H, d, J=5.2 Hz), 4.50 (2H, s), 4.40 (1H, m), 3.86 (4H, t, J=4.0 Hz) 3.69 (1H, m), 3.52 (4H, t, J=4.2), 1.25 (3H), Yield=49%

Example 21

Preparation of (S)-1-(3-chlorophenyl)-3-(3-((1-(2-((2-hydroxypropyl)amino)pyrimidin-4-yl)-1H-imidazol-2-yl)methyl)phenyl)urea

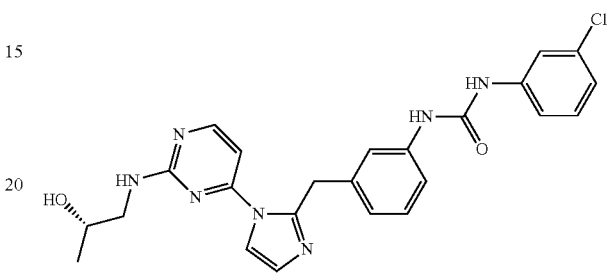

Steps 1 to 7 of Example 1 were carried out in the same manner.

After adding (S)-1-{4-[2-(3-aminobenzyl)-1H-imidazol-1-yl]pyrimidin-2-ylamino}-propan-2-ol (10 mg, 0.031 mmol) prepared in Step 7 and 1-chloro-3-isocyanatobenzene (4.8 mg, 0.031 mmol) in THF (0.4 mL), the solution was stirred for 2 hrs. After the reaction terminated, the product was extracted with ethyl acetate and washed by using saturated NaHCO$_3$ aqueous solution. After the extracted organic layer was dried with magnesium sulfate anhydrous and filtered, the solvent was eliminated under reduced pressure. The residue was purified by column chromatography (silica gel, methylene chloride MeOH=10:1), and (S)-1-(3-chlorophenyl)-3-(3-((1-(2-((2-hydroxypropyl)amino)pyrimidin-4-yl)-1H-imidazol-2-yl)methyl)phenyl)urea (Compound 10b) (7.1 mg, 48%), a product compound, was obtained.

$^1$H NMR (400 MHz, DMSO-d$_6$) δ 8.95 (1H, s), 8.78 (1H, s), 8.29 (1H, d, J=5.3 Hz), 7.60 (1H, d, J=3.02 Hz), 7.68 (1H, s), 7.49 (1H, d, J=8.7 Hz), 7.31-7.28 (4H, m), 6.98-7.01 (2H, m), 6.75 (1H, s), 6.54 (1H, d, J=6.5 Hz), 4.85 (1H, br), 4.13 (2H, s), 3.77 (2H, m), 3.24 (1H, m), 1.02 (3H, s)

Example 22

Preparation of (S)-1-(3,4-dichlorophenyl)-3-(3-((1-(2-((2-hydroxypropyl)amino)pyrimidin-4-yl)-1H-imidazol-2-yl)methyl)phenyl)urea

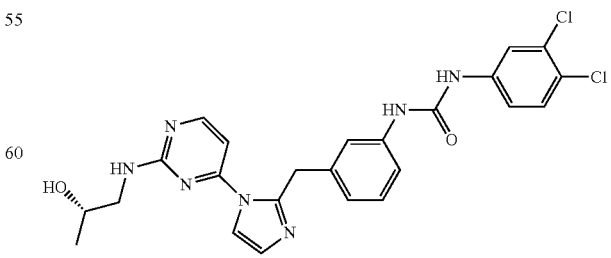

(S)-1-(3,4-dichlorophenyl)-3-(3-((1-(2-((2-hydroxypropyl)amino)pyrimidin-4-yl)-1H-imidazol-2-yl)methyl)phenyl)urea (Compound 10a), a product compound, was obtained according to the same reaction as in Example 21, except that (3,4-dichlorophenyl) isocyanate (0.031 mmol) was used instead of 1-chloro-3-isocyanatobenzene.

$^1$H NMR (400 MHz, DMSO-$d_6$) δ 8.95 (1H, s), 8.78 (1H, s), 8.32 (1H, d, J=5.3 Hz), 7.61 (1H, d, J=3.02 Hz), 7.68 (1H, s), 7.49 (1H, d, J=8.7 Hz), 7.31-7.28 (3H, m), 7.15-7.09 (2H, m), 7.01 (1H, s), 6.71 (1H, d, J=6.5 Hz), 4.68 (1H, br), 4.50 (2H, s), 3.77 (2H, m), 3.24 (1H, m), 1.03 (3H, s), Yield=38%

Example 23

Preparation of (S)-1-(3-chloro-4-(trifluoromethyl)phenyl)-3-(3-((1-(2-((2-hydroxypropyl)amino)pyrimidin-4-yl)-1H-imidazol-2-yl)methyl)phenyl)urea

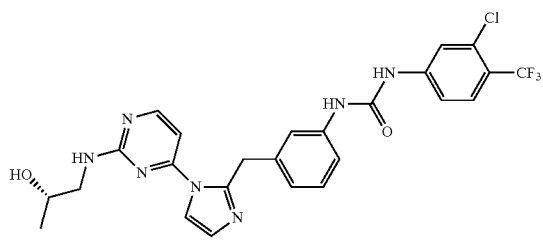 [SMILES: C[C@H](O)CNc1nccc(-n2ccnc2Cc2cccc(NC(=O)Nc3ccc(C(F)(F)F)c(Cl)c3)c2)n1]

(S)-1-(3-chloro-4-(trifluoromethyl)phenyl)-3-(3-((1-(2-((2-hydroxypropyl)amino)pyrimidin-4-yl)-1H-imidazol-2-yl)methyl)phenyl)urea (Compound 10c), a product compound, was obtained according to the same reaction as in Example 21, except that [3-chloro-4-(trifluoromethyl)phenyl] isocyanate (0.031 mmol) was used instead of 1-chloro-3-isocyanatobenzene.

$^1$H NMR (400 MHz, CDCl$_3$) δ 9.10 (2H, s), 8.32 (1H, d, J=4.8 Hz), 7.92 (1H, s), 7.54 (1H, d, J=8.8 Hz), 7.41-7.31 (4H, m), 6.99-6.96 (2H, m), 6.67 (1H, s), 6.4 (1H, d, J=4.0 Hz), 4.45 (2H, s), 4.10 (1H, m), 3.62 (1H, m), 3.35 (1H, m), 1.20 (3H, d, J=6.4 Hz), Yield=41%

Example 24

Preparation of (S)-1-(3-((4-ethylpiperazin-1-yl)methyl)-5-(trifluoromethyl)phenyl)-3-(3-((1-(2-((2-hydroxypropyl)amino)pyrimidin-4-yl)-1H-imidazol-2-yl)methyl)phenyl)urea

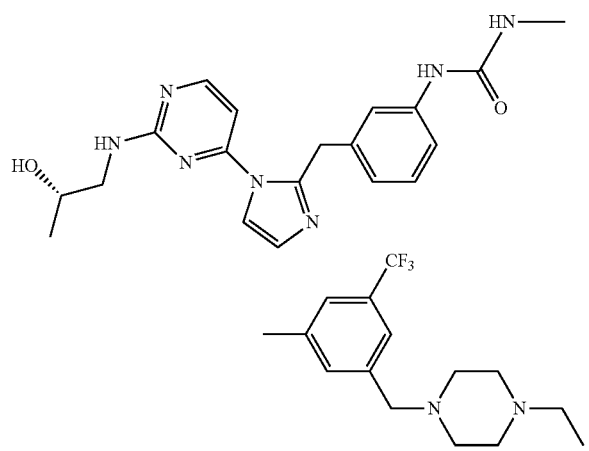

((S)-1-(3-((4-ethylpiperazin-1-yl)methyl)-5-(trifluoromethyl)phenyl)-3-(3-((1-(2-((2-hydroxypropyl)amino)pyrimidin-4-yl)-1H-imidazol-2-yl)methyl)phenyl)urea (Compound 10d), a product compound, was obtained according to the same reaction as in Example 21, except that {3-[(4-ethylpiperazin-1-yl)methyl]-5-(trifluoromethyl)phenyl} isocyanate (0.031 mmol) was used instead of 1-chloro-3-isocyanatobenzene.

$^1$H NMR (400 MHz, DMSO-$d_6$) δ 9.64 (1H, s), 9.26 (1H, s), 8.44 (1H, d, J=5.6 Hz), 7.96-7.95 (2H, m), 7.64-7.58 (2H, m), 7.50-7.46 (2H, m), 7.30 (2H, m), 7.16 (1H, t, J=7.8 Hz), 6.84 (1H, t, J=7.8 Hz), 4.80 (1H, m), 4.63 (2H, s), 3.76-3.73 (2H, m), 3.68-3.57 (4H, m), 3.11-3.04 (3H, m), 2.94-2.83 (3H, m), 2.70-2.67 (1H, m), 1.25-1.21 (6H, m), Yield=48%

Example 25

Preparation of (S)—N-(3-(1-(2-((2-hydroxypropyl)amino)pyrimidin-4-yl)-1H-imidazole-2-carbonyl)phenyl)-3-(trifluoromethyl)benzamide Step 1: Preparation of ethyl 2-(3-nitrophenyl)acetimidate

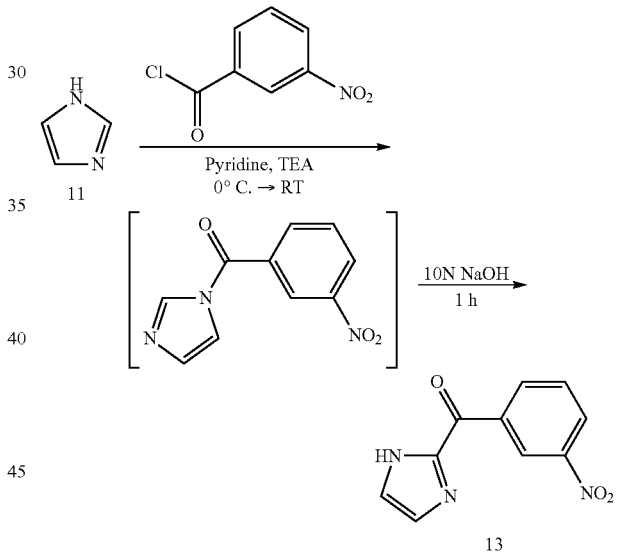

After adding pyridine (7.4 ml), TEA (2.9 g) and Compound 11 (1.0 g) were added thereto in order and 3-nitro benzoyl chloride (5.4 g) was slowly added thereto at 0° C. And then, the solution was stirred at room temperature and the color of the reactant was changed from yellow to dark brown while 10 mins passed. After stirring the solution for about 3 hrs, the intermediate product was formed and, without a separate purification, 10 N NaOH (3.7 ml) was directly added thereto and Compound 13 was synthesized by stirring the same for about 1 hr at 100° C. After the reaction terminated, the product was cooled to room temperature and diluted with a small quantity of H$_2$O, and pH of the solution was adjusted to about 6 by slowly adding 6 N HCl aqueous solution thereto. The compound adjusted to about pH 6 was cooled in an ice bath for about 30 mins and filtered by using H$_2$O and hexane solvent. After drying the filtered solid, it was purified and separated by column chromatography (silicagel, ethylacetate:Hexane=2:1), and a product Compound 13 (1.9 g, 62%) was obtained.

¹H NMR (400 MHz, DMSO-d₆) δ 13.70 (s, 1H), 9.39 (s, 1H), 8.83 (d, J=7.6 Hz, 1H), 8.51-8.49 (m, 1H), 7.88 (t, J=8 Hz, 1H), 7.62 (s, 2H), 7.38 (s, 1H)

Steps 2 to 5: Preparation of (S)-(3-aminophenyl)(1-(2-((2-hydroxypropyl)amino)pyrimidin-4-yl)-1H-imidazol-2-yl)methanone

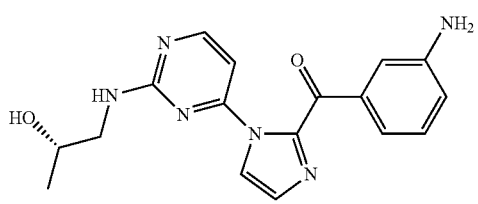

A product Compound 16 was obtained by carrying out Steps 2 to 5 similar to Steps 4 to 7 of Example 1 respectively.

¹H NMR (400 MHz, DMSO-d₆) δ 8.79 (s, 1H), 8.39 (s, 1H), 7.78-7.46 (m, 5H), 7.24 (d, J=6.8 Hz, 2H), 4.25 (s, 1H), 3.92 (s, 1H), 2.87 (s, 1H), 2.68 (s, 1H), 0.78 (s, 3H)

Step 6: Preparation of (S)—N-(3-(1-(2-((2-hydroxypropyl)amino)pyrimidin-4-yl)-1H-imidazole-2-carbonyl)phenyl)-3-(trifluoromethyl)benzamide

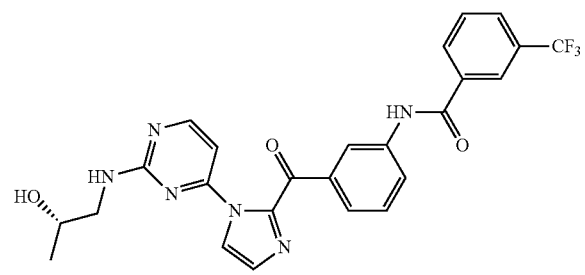 [SMILES: C[C@H](O)CNc1nccc(-n2ccnc2C(=O)c2cccc(NC(=O)c3cccc(C(F)(F)F)c3)c2)n1]

After dissolving (S)-(3-aminophenyl)(1-(2-((2-hydroxypropyl)amino)pyrimidin-4-yl)-1H-imidazol-2-yl)methanone (10.5 mg, 0.031 mmol) prepared in Step 5, 3-(trifluoromethyl)benzoic acid (6.0 mg, 0.031 mmol), EDCI (8.9 mg, 0.047 mmol), HOBt (6.28 mg, 0.047 mmol), and TEA (6.27 mg, 0.062 mmol) in DMF (0.4 mL), the solution was stirred for about 5 hrs at 50° C. After the reaction terminated, ethyl acetate was added thereto and the product was washed with saturated NaHCO₃ aqueous solution. After the organic layer was dried with magnesium sulfate anhydrous and filtered, the solvent was eliminated under reduced pressure. The residue was purified by column chromatography (silica gel, methylene chloride:MeOH=10:1), and ((S)—N-(3-(1-(2-((2-hydroxypropyl)amino)pyrimidin-4-yl)-1H-imidazole-2-carbonyl)phenyl)-3-(trifluoromethyl)benzamide (Compound 18a), a product compound, was obtained.

¹H NMR (400 MHz, DMSO-d₆) δ 10.70 (s, 1H), 8.40 (s, 1H), 8.31 (t, J=8.6 Hz, 2H), 8.15 (d, J=6.5 Hz, 1H), 8.05 (s, 1H), 7.99 (d, J=7.7 Hz, 1H), 7.81 (t, J=7.9 Hz, 1H), 7.32 (s, 1H), 7.19 (s, 1H), 6.88 (s, 1H), 4.46 (s, 1H), 3.50 (s, 1H), 2.81 (s, 1H), 2.62 (s, 1H), 0.71 (s, 3H), Yield=27%

Example 26

Preparation of (S)—N-(3-(1-(2-((2-hydroxypropyl)amino)pyrimidin-4-yl)-1H-imidazole-2-carbonyl)phenyl)-5-(4-methoxyphenyl)furan-2-carboxamide

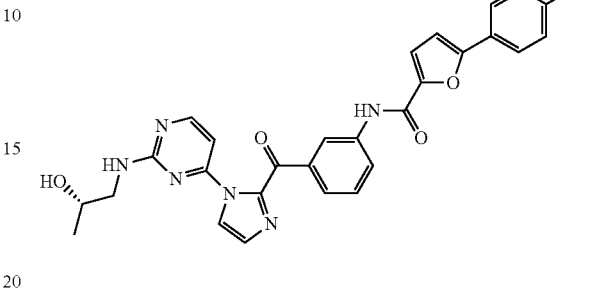

Steps 1 to 5 of Example 25 were carried out in the same manner. In the next step, (S)—N-(3-(1-(2-((2-hydroxypropyl)amino)pyrimidin-4-yl)-1H-imidazole-2-carbonyl)phenyl)-5-(4-methoxyphenyl)furan-2-carboxamide (Compound 18b), a product compound, was obtained according to the same reaction as in Example 25, except that 5-(4-methoxyphenyl)furan-2-carboxylic acid (0.031 mmol) was used instead of 3-(trifluoromethyl)benzoic acid.

¹H NMR (400 MHz, DMSO-d₆) δ 10.35 (s, 1H), 8.41 (d, J=4.4 Hz, 2H), 8.15 (s, 1H), 8.08 (s, 1H), 7.54 (s, 2H), 7.41 (d, J=3.6 Hz, 1H), 7.07-7.02 (m, 5H), 4.46 (s, 1H), 3.67 (s, 3H), 3.49 (s, 1H), 2.82 (s, 1H), 2.64 (s, 1H), 0.73 (s, 3H). Yield=62%

Example 27

Preparation of (S)—N-(3-(1-(2-((2-hydroxypropyl)amino)pyrimidin-4-yl)-1H-imidazole-2-carbonyl)phenyl)-3-morpholino-5-(trifluoromethyl)benzamide

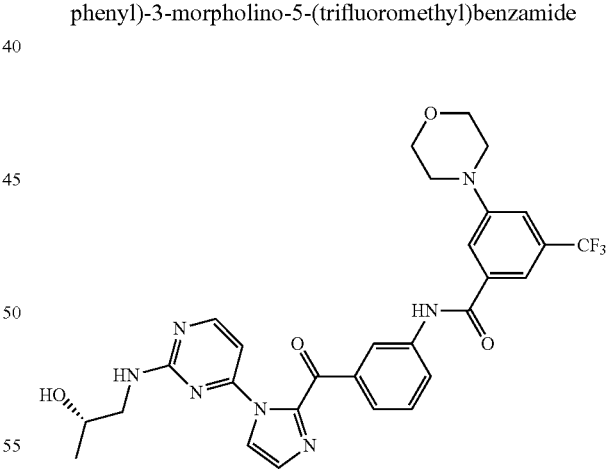

Steps 1 to 5 of Example 25 were carried out in the same manner. In the next step, (S)—N-(3-(1-(2-((2-hydroxypropyl)amino)pyrimidin-4-yl)-1H-imidazole-2-carbonyl)phenyl)-3-morpholino-5-(trifluoromethyl)benzamide (Compound 18c), a product compound, was obtained according to the same reaction as in Example 25, except that 3-(morpholin-4-yl)-5-(trifluoromethyl)benzoic acid (0.031 mmol) was used instead of 3-(trifluoromethyl)benzoic acid.

¹H NMR (400 MHz, DMSO-d₆) δ 10.58 (s, 1H), 8.40 (d, J=5.2 Hz, 2H), 8.13 (d, J=6.8 Hz, 1H), 7.23-7.66 (m, 3H), 7.57 (t, J=7.8 Hz, 1H), 7.40 (s, 1H), 7.21 (s, 1H), 6.87 (s, 1H), 4.47 (s, 1H), 3.76 (t, J=4.6 Hz, 5H), 3.51 (s, 1H), 3.28 (t, J=5.2 Hz, 3H), 2.80 (s, 1H), 0.71 (s, 3H). Yield=45%

Example 28

Preparation of (S)—N-(3-(1-(2-((2-hydroxypropyl)amino)pyrimidin-4-yl)-1H-imidazole-2-carbonyl)phenyl)-3-(4-methylpiperazin-1-yl)-5-(trifluoromethyl)benzamide

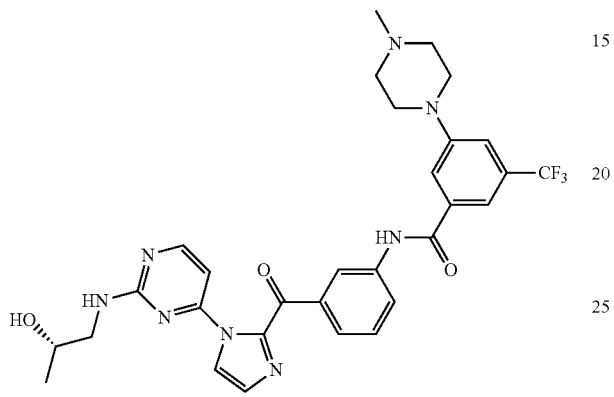

Steps 1 to 5 of Example 25 were carried out in the same manner. In the next step, (S)—N-(3-(1-(2-((2-hydroxypropyl)amino)pyrimidin-4-yl)-1H-imidazole-2-carbonyl)phenyl)-3-(4-methylpiperazin-1-yl)-5-(trifluoromethyl)benzamide (Compound 18d), a product compound, was obtained according to the same reaction as in Example 25, except that 3-(4-methylpiperazin-1-yl)-5-(trifluoromethyl)benzoic acid (0.031 mmol) was used instead of 3-(trifluoromethyl)benzoic acid.

$^1$H NMR (400 MHz, DMSO-d$_6$) δ 10.16 (s, 1H), 8.41-8.36 (m, 1H), 8.09 (t, J=4.4 Hz, 1H), 7.77-7.70 (m, 3H), 7.61-7.52 (m, 2H), 7.43-7.32 (m, 1H), 7.22 (s, 1H), 7.11 (s, 1H), 6.86 (d, J=5.6 Hz, 1H), 4.49 (s, 1H), 4.03-3.99 (m, 2H), 3.54 (m, 5H), 2.87 (m, 5H), 1.18 (s, 3H), 0.70 (s, 3H)

Example 29

Preparation of (S)-4-chloro-N-(3-(1-(2-((2-hydroxypropyl)amino)pyrimidin-4-yl)-1H-imidazole-2-carbonyl)phenyl)benzamide

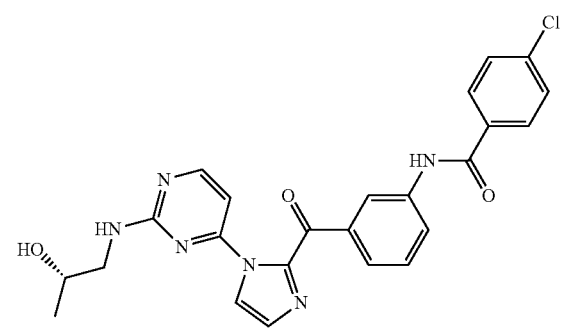 [SMILES: C[C@H](O)CNc1nccc(-n2ccnc2C(=O)c2cccc(NC(=O)c3ccc(Cl)cc3)c2)n1]

Steps 1 to 5 of Example 25 were carried out in the same manner. In the next step, (S)-4-chloro-N-(3-(1-(2-((2-hydroxypropyl)amino)pyrimidin-4-yl)-1H-imidazole-2-carbonyl)phenyl)benzamide (Compound 18e), a product compound, was obtained according to the same reaction as in Example 25, except that 4-chlorobenzoic acid (0.031 mmol) was used instead of 3-(trifluoromethyl)benzoic acid.

$^1$H NMR (400 MHz, DMSO-d$_6$) δ 10.54 (s, 1H), 8.52-8.39 (m, 3H), 8.13-8.00 (m, 4H), 7.62-7.54 (m, 3H), 7.33 (s, 1H), 6.88 (s, 1H), 4.37 (s, 1H), 3.68 (s, 1H), 3.22 (s, 1H), 2.87 (m, 1H), 0.72 (s, 3H). Yield=49%

Example 30

Preparation of (S)-3-chloro-N-(3-(1-(2-((2-hydroxypropyl)amino)pyrimidin-4-yl)-1H-imidazole-2-carbonyl)phenyl)benzamide

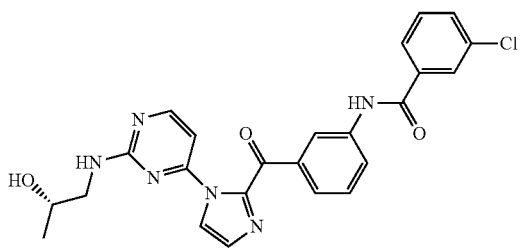 [SMILES: C[C@H](O)CNc1nccc(-n2ccnc2C(=O)c2cccc(NC(=O)c3cccc(Cl)c3)c2)n1]

Steps 1 to 5 of Example 25 were carried out in the same manner. In the next step, (S)-3-chloro-N-(3-(1-(2-((2-hydroxypropyl)amino)pyrimidin-4-yl)-1H-imidazole-2-carbonyl)phenyl)benzamide (Compound 18f), a product compound, was obtained according to the same reaction as in Example 25, except that 3-chlorobenzoic acid (0.031 mmol) was used instead of 3-(trifluoromethyl)benzoic acid.

$^1$H NMR (400 MHz, DMSO-d$_6$) δ 10.57 (s, 1H), 8.40 (s, 2H), 8.13-7.82 (m, 4H), 7.68 (d, J=7.6 Hz, 1H), 7.59-7.54 (m, 2H), 7.32 (s, 1H), 7.19 (s, 1H), 6.81 (s, 1H), 4.49 (s, 1H), 3.17 (s, 1H), 2.81 (s, 1H), 0.84 (s, 3H). Yield=40%

Example 31

Preparation of (S)-1-(3,4-dichlorophenyl)-3-(3-(1-(2-((2-hydroxypropyl)amino)pyrimidin-4-yl)-1H-imidazole-2-carbonyl)phenyl)urea

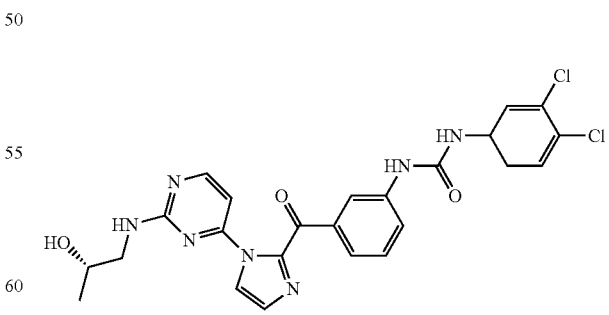

Steps 1 to 5 of Example 25 were carried out in the same manner. In the next step, (S)-1-(3,4-dichlorophenyl)-3-(3-(1-(2-((2-hydroxypropyl)amino)pyrimidin-4-yl)-1H-imidazole-2-carbonyl)phenyl)urea (Compound 19a), a product compound, was obtained according to the same reaction as in Example 25, except that (3,4-dichlorophenyl) isocyanate (0.031 mmol) was used instead of 3-(trifluoromethyl)benzoic acid.

¹H NMR (400 MHz, DMSO-d₆) δ 9.16 (s, 1H), 9.08 (s, 1H), 8.39 (d, J=4.4 Hz, 1H), 8.09 (s, 1H), 8.02 (s, 1H), 7.86 (d, J=2.4 Hz, 1H), 7.75 (d, J=7.2 Hz, 1H), 7.52-7.43 (m, 2H), 7.35-7.30 (m, 2H), 7.15 (s, 1H), 6.91 (s, 1H), 4.47 (s, 1H), 3.73 (s, 1H), 2.80 (s, 1H), 2.64 (s, 1H), 0.71 (s, 3H). Yield=44%

Example 32

Preparation of (S)-1-(4-chlorophenyl)-3-(3-(1-(24 (2-hydroxypropyl)amino)pyrimidin-4-yl)-1H-imidazole-2-carbonyl)phenyl)urea

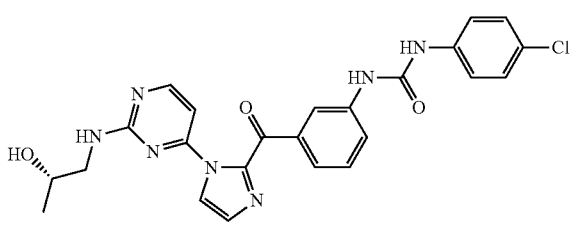 [SMILES: C[C@H](O)CNc1nccc(-n2ccnc2C(=O)c2cccc(NC(=O)Nc3ccc(Cl)cc3)c2)n1]

Steps 1 to 5 of Example 25 were carried out in the same manner. In the next step, (S)-1-(4-chlorophenyl)-3-(3-(1-(2-((2-hydroxypropyl)amino)pyrimidin-4-yl)-1H-imidazole-2-carbonyl)phenyl)urea (Compound 19b), a product compound, was obtained according to the same reaction as in Example 25, except that (4-chlorophenyl) isocyanate (0.031 mmol) was used instead of 3-(trifluoromethyl)benzoic acid.

¹H NMR (400 MHz, DMSO-d₆) δ 9.00 (s, 1H), 8.83 (s, 1H), 8.39 (s, 1H), 8.08-7.98 (m, 2H), 7.74-7.63 (m, 1H), 7.59-7.47 (m, 3H), 7.31 (d, J=5.6 Hz, 3H), 7.16 (s, 1H), 6.85 (s, 1H), 4.45 (s, 1H), 3.61 (s, 1H), 2.83 (s, 1H), 2.65 (s, 1H), 0.72 (s, 3H). Yield=57%

Example 33

Preparation of (S)-4-chloro-N-(4-(1-(2-((2-hydroxypropyl)amino)pyrimidin-4-yl)-1H-imidazole-2-carbonyl)phenyl)benzamide Steps 1 to 5: Preparation of (S)-(4-aminophenyl)(1-(2-((2-hydroxypropyl)amino)pyrimidin-4-yl)-1H-imidazol-2-yl)methanone

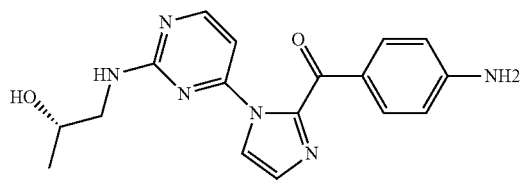

16'

A product Compound 16' was obtained according to the same reaction as Steps 1 to 5 of Example 25, except that 4-nitrobenzoyl chloride was used instead of 3-nitro benzoyl chloride in Step 1 of Example 25.

¹H NMR (400 MHz, DMSO-d₆) δ 13.67 (s, 1H), 8.64 (d, J=7.2 Hz, 2H), 8.38 (d, J=7.2 Hz, 2H), 7.60 (s, 1H), 7.35 (s, 1H). Yield=51%

Step 6: Preparation of (S)-4-chloro-N-(4-(1-(2-((2-hydroxypropyl)amino)pyrimidin-4-yl)-1H-imidazole-2-carbonyl)phenyl)benzamide

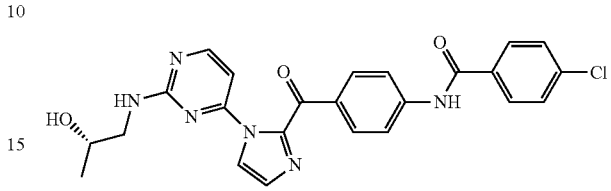

After dissolving (S)-(4-aminophenyl)(1-(2-((2-hydroxypropyl)amino)pyrimidin-4-yl)-1H-imidazol-2-yl)methanone (10.5 mg, 0.031 mmol) prepared in Step 5, 4-chlorobenzoic acid (4.85 mg, 0.031 mmol), EDCI (8.9 mg, 0.047 mmol), HOBt (6.28 mg, 0.047 mmol), and TEA (6.27 mg, 0.062 mmol) in DMF (0.4 mL), the solution was stirred for about 5 hrs at 50° C. After the reaction terminated, ethyl acetate was added thereto and the product was washed with saturated NaHCO₃ aqueous solution. After the organic layer was dried with magnesium sulfate anhydrous and filtered, the solvent was eliminated under reduced pressure. The residue was purified by column chromatography (silica gel, methylene chloride:MeOH=10:1), and (S)-4-chloro-N-(4-(1-(2-((2-hydroxypropyl)amino)pyrimidin-4-yl)-1H-imidazole-2-carbonyl)phenyl)benzamide (Compound 18g), a product compound, was obtained.

¹H NMR (400 MHz, DMSO-d₆) δ 10.70 (s, 1H), 8.39 (dd, J=6.8, 4.8 Hz, 1H), 8.11-7.99 (m, 4H), 7.64 (d, J=8.8 Hz, 2H), 7.35-7.09 (m, 2H), 6.83 (s, 1H), 6.58 (d, J=8.4 Hz, 1H), 6.27 (s, 1H), 4.56 (s, 1H), 3.73 (s, 1H) 2.88 (s, 1H), 2.72 (s, 1H), 0.84 (s, 3H). Yield=33%

Example 34

Preparation of (S)-3-chloro-N-(4-(1-(2-((2-hydroxypropyl)amino)pyrimidin-4-yl)-1H-imidazole-2-carbonyl)phenyl)benzamide

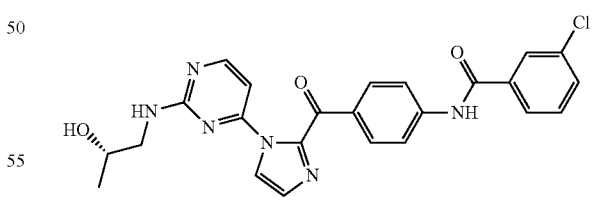

Steps 1 to 5 of Example 33 were carried out in the same manner. In the next step, (S)-3-chloro-N-(4-(1-(2-((2-hydroxypropyl)amino)pyrimidin-4-yl)-1H-imidazole-2-carbonyl)phenyl)benzamide (Compound 18h), a product compound, was obtained according to the same reaction as in Example 33, except that 3-chlorobenzoic acid (0.031 mmol) was used instead of 4-chlorobenzoic acid.

¹H NMR (400 MHz, DMSO-d₆) δ 10.71 (s, 1H), 8.39-8.23 (m, 2H), 8.02-7.92 (m, 5H), 7.70 (d, J=7.6 Hz, 1H), 7.60 (d, J=8 Hz, 1H), 7.30 (s, 1H), 7.18 (s, 1H), 6.85 (s, 1H), 4.76 (s, 1H), 3.37 (s, 1H) 2.81 (s, 2H), 0.84 (s, 3H). Yield=13%

Example 35

Preparation of (S)—N-(4-(1-(2-((2-hydroxypropyl)amino)pyrimidin-4-yl)-1H-imidazole-2-carbonyl)phenyl)-3-morpholino-5-(trifluoromethyl)benzamide

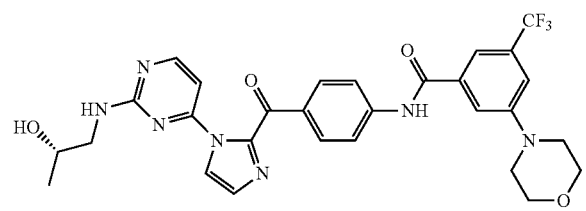

Steps 1 to 5 of Example 33 were carried out in the same manner. In the next step, (S)—N-(4-(1-(2-((2-hydroxypropyl)amino)pyrimidin-4-yl)-1H-imidazole-2-carbonyl)phenyl)-3-morpholino-5-(trifluoromethyl)benzamide (Compound 18i), a product compound, was obtained according to the same reaction as in Example 33, except that 3-(morpholin-4-yl)-4-(trifluoromethyl)benzoic acid (0.031 mmol) was used instead of 4-chlorobenzoic acid.

$^1$H NMR (400 MHz, DMSO-d$_6$) δ 10.60 (s, 1H), 8.33 (d, J=4.8 Hz, 1H), 7.83 (d, J=8 Hz, 1H), 7.74 (s, 1H), 7.69-7.57 (m, 1H), 7.53-7.52 (m, 1H), 7.41 (s, 1H), 7.19 (s, 1H), 6.58 (s, 1H), 6.29 (s, 1H), 4.26 (s, 1H), 3.72-3.65 (m, 5H), 3.38-3.21 (m, 5H) 2.70 (s, 1H), 2.66 (s, 1H), 0.84 (s, 3H). Yield=7%

Example 36

Preparation of (S)—N-(4-(1-(2-((2-hydroxypropyl)amino)pyrimidin-4-yl)-1H-imidazole-2-carbonyl)phenyl)-3-(4-methylpiperazin-1-yl)-5-(trifluoromethyl)benzamide

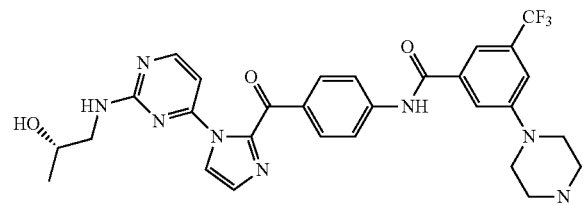 [SMILES: C[C@H](O)CNc1nccc(-n2ccnc2C(=O)c2ccc(NC(=O)c3cc(N4CCOCC4)cc(C(F)(F)F)c3)cc2)n1]

Steps 1 to 5 of Example 33 were carried out in the same manner. In the next step, (S)—N-(4-(1-(2-((2-hydroxypropyl)amino)pyrimidin-4-yl)-1H-imidazole-2-carbonyl)phenyl)-3-(4-methylpiperazin-1-yl)-5-(trifluoromethyl)benzamide (Compound 18j), a product compound, was obtained according to the same reaction as in Example 33, except that 3-(4-methylpiperazin-1-yl)-5-(trifluoromethyl)benzoic acid (0.031 mmol) was used instead of 4-chlorobenzoic acid.

$^1$H NMR (400 MHz, DMSO-d$_6$) δ 10.60 (s, 1H), 8.70 (s, 1H), 8.35-8.18 (m, 2H), 8.105 (d, J=8 Hz, 2H), 7.74 (s, 1H), 7.85-7.74 (m, 2H), 7.58-7.55 (m, 2H), 7.43 (s, 1H), 7.24 (s, 1H), 4.11-4.09 (m, 6H), 3.71-3.68 (m, 3H), 2.88 (s, 1H), 2.62 (s, 1H), 0.83 (d, J=2.8 Hz, 3H). Yield=5.4%

Example 37

Preparation of (S)-4-chloro-N-(4-(1-(2-((2-hydroxypropyl)amino)pyrimidin-4-yl)-1H-imidazole-2-carbonyl)phenyl)-3-(trifluoromethyl)benzamide

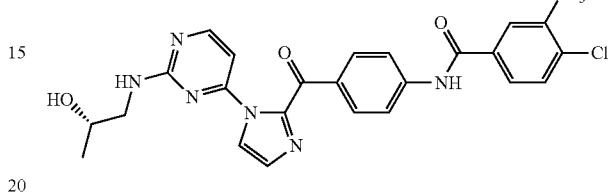

Steps 1 to 5 of Example 33 were carried out in the same manner. In the next step, (S)-4-chloro-N-(4-(1-(2-((2-hydroxypropyl)amino)pyrimidin-4-yl)-1H-imidazole-2-carbonyl)phenyl)-3-(trifluoromethyl)benzamide (Compound 18k), a product compound, was obtained according to the same reaction as in Example 33, except that 4-chloro-3-(trifluoromethyl)benzoic acid (0.031 mmol) was used instead of 4-chlorobenzoic acid.

$^1$H NMR (400 MHz, DMSO-d$_6$) δ 10.86 (s, 1H), 8.45-8.34 (m, 2H), 8.28 (s, 1H), 8.12-7.92 (m, 5H), 7.36-7.22 (m, 2H), 6.84 (s, 1H), 5.70 (s, 1H), 3.09 (s, 1H), 2.82 (s, 1H), 0.95 (s, 3H). Yield=27.5%

Example 38

Preparation of (S)-1-(4-chloro-3-(trifluoromethyl)phenyl)-3-(4-(1-(2-((2-hydroxypropyl)amino)pyrimidin-4-yl)-1H-imidazole-2-carbonyl)phenyl)urea

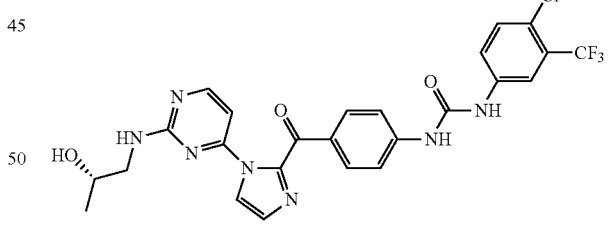

Steps 1 to 5 of Example 33 were carried out in the same manner. In the next step, (S)-1-(4-chloro-3-(trifluoromethyl)phenyl)-3-(4-(1-(2-((2-hydroxypropyl)amino)pyrimidin-4-yl)-1H-imidazole-2-carbonyl)phenyl)urea (Compound 19c), a product compound, was obtained according to the same reaction as in Example 33, except that [4-chloro-3-(trifluoromethyl)phenyl]isocyanate (0.031 mmol) was used instead of 4-chlorobenzoic acid.

$^1$H NMR (400 MHz, DMSO-d$_6$) δ 9.97 (s, 1H), 8.48-8.35 (m, 1H), 8.10-7.91 (m, 3H), 7.66-7.57 (m, 4H), 7.26 (d, J=4 Hz, 1H), 6.79 (s, 1H), 6.58 (d, J=3.2 Hz, 1H), 6.28 (s, 1H), 4.62 (s, 1H), 3.10 (s, 1H), 2.98 (s, 1H), 0.96 (s, 3H). Yield=12%

Example 39

Preparation of (S)-1-(3,4-dichlorophenyl)-3-(4-(1-(2-((2-hydroxypropyl)amino)pyrimidin-4-yl)-1H-imidazole-2-carbonyl)phenyl)urea

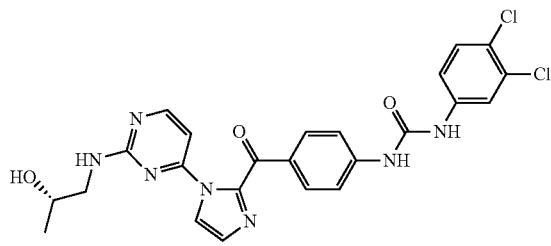 [SMILES: C[C@H](O)CNc1nccc(-n2ccnc2C(=O)c2ccc(NC(=O)Nc3ccc(Cl)c(Cl)c3)cc2)n1]

Steps 1 to 5 of Example 33 were carried out in the same manner. In the next step, (S)-1-(3,4-dichlorophenyl)-3-(4-(1-(2-((2-hydroxypropyl)amino)pyrimidin-4-yl)-1H-imidazole-2-carbonyl)phenyl)urea (Compound 19d), a product compound, was obtained according to the same reaction as in Example 33, except that (3,4-dichlorophenyl) isocyanate (0.031 mmol) (0.031 mmol) was used instead of 4-chlorobenzoic acid.

$^1$H NMR (400 MHz, DMSO-$d_6$) δ 9.81 (s, 1H), 8.39 (d, J=4.4 Hz, 1H), 7.97 (d, J=7.2 Hz, 1H), 7.91-7.76 (m, 2H), 7.64-7.40 (m, 2H), 7.19 (s, 1H), 6.77 (d, J=8.4 Hz, 1H), 6.59 (d, J=8.8 Hz, 1H), 6.29 (s, 1H), 4.75 (s, 1H), 3.48 (s, 1H), 2.98 (s, 1H), 2.67 (s, 1H), 0.83 (s, 3H). Yield=17.7%

Comparative Example 1

Sorafenib of the following Structural Formula, purchased from Sigma Aldrich, was prepared as a reference standard.

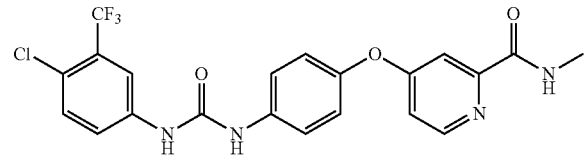 [SMILES: CNC(=O)c1cc(Oc2ccc(NC(=O)Nc3ccc(Cl)c(C(F)(F)F)c3)cc2)ccn1]

Experimental Examples

Evaluation on the Antiproliferative Activity to A375P Human Melanoma Cell Line and U937 Human Leukemic Monocyte Lymphoma Cell Line The antiproliferative activity of the compounds of Examples to A375P human melanoma cell line and U937 human leukemic monocyte lymphoma cell line are evaluated and listed in the following Table 1.

TABLE 1

| Examples | Compound | A375P (GI$_{50}$, Unit: μM) | U937 (GI$_{50}$, Unit: μM) |
| --- | --- | --- | --- |
| Example 1 | Compound 9a | 12.3 | >30 |
| Example 2 | Compound 9b | NA | 16.8 |
| Example 4 | Compound 9d | 7.45 | >30 |
| Example 5 | Compound 9e | 6.39 | 25.8 |
| Example 6 | Compound 9f | 10.2 | >30 |
| Example 7 | Compound 9g | NA | 23.8 |
| Example 9 | Compound 9i | >30 | 18.5 |
| Example 10 | Compound 9j | 8.92 | NA |
| Example 11 | Compound 9k | 11.2 | 10.0 |
| Example 12 | Compound 9l | 0.6 | 1.68 |
| Example 15 | Compound 9o | NA | 10.0 |
| Example 16 | Compound 9p | NA | 23.6 |
| Example 17 | Compound 9q | 3.97 | 3.24 |
| Example 19 | Compound 9s | 3.3 | 6.83 |
| Example 20 | Compound 9t | 6.6 | 9.7 |
| Example 21 | Compound 10b | 19.2 | 1.73 |
| Example 22 | Compound 10a | 26.2 | 15.3 |
| Example 23 | Compound 10c | 1.82 | 2.73 |
| Example 25 | Compound 18a | >30 | 3.78 |
| Example 26 | Compound 18b | 9.39 | 2.55 |
| Example 27 | Compound 18c | NA | 4.9 |
| Example 28 | Compound 18d | 27.8 | NA |
| Example 33 | Compound 18g | 7.07 | NA |
| Example 34 | Compound 18h | 5.92 | NA |
| Example 36 | Compound 18j | >30 | 14.7 |
| Example 38 | Compound 19c | >30 | 7.45 |
| Example 39 | Compound 19d | >30 | 11.6 |
| Comparative Example 1 | Sorafenib | 3.4 | 2.74 |

Generally, the antiproliferative activity to A375P human melanoma cell line is stronger than that to U937 human leukemic monocyte lymphoma cell line. The tail group of $R_1$ seems to be important as the moiety that influences the compounds of Examples of the present invention, and it shows that the activity of the compounds of the Examples of the present invention is more sensitive to secondary hydrophobic pocket.

Among the compounds of the Examples, particularly, Example 12 (Compound 9l), Example 19 (Compound 9s), and Example 23 (Compound 10c) showed large potencies to both of A375P and U937 cell lines. Above all, Example 12 (Compound 9l) and Example 23 (Compound 10c) showed better potencies than Sorafenib, and Example 19 (Compound 9s) demonstrated a similar potency to Sorafenib against A375P with showing a micromolar scale IC$_{50}$ value.

Evaluation on the Enzymatic Activities to Various Kinases

To Compound 10c of Example 23, kinase panel screening was carried out to 32 kinds of kinases in 10 μM concentration and the results are listed in the following Table 2.

TABLE 2

| Kinase | Inhibition Rate (Unit: %) |
| --- | --- |
| ABL1 | 6.9 |
| AKT1 | 12.9 |
| ALK | 4.9 |
| Aurora A | 17.6 |
| BRAF | 99.9 |
| BRAF (V600E) | 96.1 |
| BTK | 0 |
| c-Kit | 63.8 |
| c-MET | 17.6 |
| c-Src | 2.1 |
| CDK1/cyclin B | 34.8 |
| EGFR | 0 |
| ERK1 | 0 |
| FAK/PTK2 | 1.2 |
| FGFR3 | 3.5 |
| FLT3 | 68.4 |

TABLE 2-continued

| Kinase | Inhibition Rate (Unit: %) |
|---|---|
| FMS | 33.6 |
| GSK3b | 34.5 |
| IGF1R | 0 |
| JAK3 | 0 |
| JNK3 | 0 |
| LCK | 5.8 |
| LYN | 8.1 |
| MEK1 | 0 |
| mTOR/FRAP1 | 0 |
| P38a/MAPK14 | 94.3 |
| PKA | 0 |
| PLK1 | 9.9 |
| RAF1 | 98.7 |
| RON/MST1R | 0.42 |
| ROS/ROS1 | 0.73 |
| SYK | 0 |

Referring to Table 2, it is revealed that the compound of Example 23 is the selective RAF inhibitor having highest selectivity. While the compound of Example 23 showed the inhibition rate of 99% to BRAF, BRAF V600E, and CRAF in 10 μM concentration, it showed the inhibition rate less than 30% to most other kinases except cKit (KIT) and p38a (MAPK14).

Furthermore, the enzymatic activity ($IC_{50}$) of the compound of Example 23 and other known two amide derivative compounds (GW507 and SB202190) to wild-type BRAF, BRAF V600E, CRAF, and p38a kinases were evaluated and the results are listed in the following Table 3.

TABLE 3

| | $IC_{50}$ (Unit: nM) | | |
|---|---|---|---|
| | Example 23 | GW5074 | SB202190 |
| BRAF | 186 | 10.71 | ND |
| BRAF (V600E) | 38.3 | 5.4 | ND |
| P38a/MAPK14 | 571 | ND | 8.66 |
| cRAF1 | 8.79 | 4.4 | ND |

Referring to Table 3, it is clearly proved that the compound of Example 23 is a therapeutic agent that is very selective to BRAF V600E and CRAF inhibitor and applicable to melanoma, compared to known amide derivatives.

Considering that BRAF V600E and CRAF are concerned with the progression of disease and the cell proliferation in a subset of melanoma, the compound of Example 23 that is a dual RAF-kinase inhibitor seems to be very effective in the therapy for melanoma. The compound of Example 23 is expected to be especially valuable because its selectivity to the mutants rather than wild-type BRAF is far better than known compounds.

What is claimed is:

1. An imidazole-1-yl pyrimidine derivative represented by the following Chemical Formula 1, or a pharmaceutically acceptable salt thereof:

[Chemical Formula]

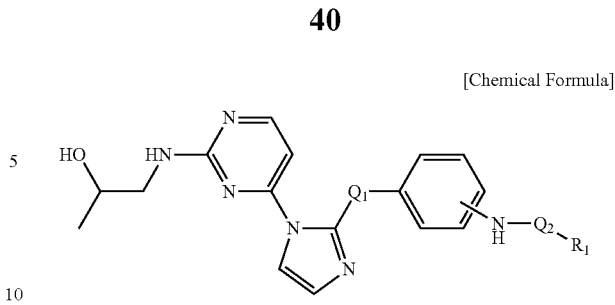

in Chemical Formula 1,
Q₁ is —$CH_2$— or —CO—;
Q₂ is —CO— or —CONH—;
R₁ is a $C_6$-$C_{20}$ aryl, a $C_7$-$C_{20}$ alkylaryl, a $C_7$-$C_{20}$ arylalkyl, a $C_5$-$C_{20}$ heteroaryl, a $C_3$-$C_{20}$ cycloalkyl, or a $C_3$-$C_{20}$ heterocycloalkyl, wherein said R₁ is substituted with a halogen, a halogenated alkyl, hydroxyl group, carbonyl group, cyano group, alkoxy group, or a $C_3$-$C_{20}$ heterocycloalkyl or not.

2. The imidazole-1-yl pyrimidine derivative, or the pharmaceutically acceptable salt thereof according to claim 1, wherein R₁ is chlorophenyl, dichlorophenyl, fluorophenyl, dimethylphenyl, quinolinyl, pyridinyl, pyrazinyl, 1H-benzotriazol-5-yl, biphenyl-2-yl, biphenyl-4-yl, trifluoromethylphenyl, bis(4-chlorophenyl)methyl, 2-chloro-5-(4-chlorobenzyl)phenyl, biphenyl-4-ylmethyl, 1-acetylpiperidin-4-yl, 5-(4-methoxyphenyl)furan-2-yl, 2-[(2-cyanophenyl)sulfanyl]phenyl, 6-hydroxy-2,5,7,8-tetramethyl-3,4-dihydro-2H-chromen-2-yl, bis(4-chlorophenyl)methyl, 4-(morpholin-4-yl)-3-(trifluoromethyl)phenyl, 3-(morpholin-4-yl)-4-(trifluoromethyl)phenyl, 3-(morpholin-4-yl)-5-(trifluoromethyl)phenyl, 1H-indol-3-yl-methyl, dihydro-1H-indol-2-yl, 3-chloro-4-(trifluoromethyl)phenyl, 3-(4-methylpiperazin-1-yl)-5-(trifluoromethyl)phenyl, 4-[(4-ethylpiperazin-1-yl)methyl]-3-(trifluoromethyl)phenyl, or 3-(4-methylpiperazin-1-yl)-5-(trifluoromethyl)phenyl.

3. The imidazole-1-yl pyrimidine derivative, or the pharmaceutically acceptable salt thereof according to claim 1, wherein the compound of Chemical Formula 1 is selected from the group consisting of the following compounds:

(S)—N-(3-((1-(2-((2-hydroxypropyl)amino)pyrimidin-4-yl)-1H-imidazol-2-yl)methyl)phenyl)-3-(4-methylpiperazin-1-yl)-5-(trifluoromethyl)benzamide, (S)—N-(3-((1-(2-((2-hydroxypropyl)amino)pyrimidin-4-yl)-1H-imidazol-2-yl)methyl)phenyl)-3,5-dimethylbenzamide, (S)—N-(4-((1-(2-((2-hydroxypropyl)amino)pyrimidin-4-yl)-1H-imidazol-2-yl)methyl)phenyl)pyrazine-2-carboxamide, (S)-2-(2-fluorophenyl)-N-(3-((1-(2-((2-hydroxypropyl)amino)pyrimidin-4-yl)-1H-imidazol-2-yl)methyl)phenyl)acetamide, (S)—N-(3-((1-(2-((2-hydroxypropyl)amino)pyrimidin-4-yl)-1H-imidazol-2-yl)methyl)phenyl)-1-phenyl-5-(trifluoromethyl)-1H-pyrazole-4-carboxamide, (S)-4-chloro-N-(3-((1-(2-((2-hydroxypropyl)amino)pyrimidin-4-yl)-1H-imidazol-2-yl)methyl)phenyl)benzamide, (S)—N-(3-((1-(2-((2-hydroxypropyl)amino)pyrimidin-4-yl)-1H-imidazol-2-yl)methyl)phenyl)quinoline-2-carboxamide, (S)—N-(3-((1-(2-((2-hydroxypropyl)amino)pyrimidin-4-yl)-1H-imidazol-2-yl)methyl)phenyl)-1H-indole-3-carboxamide, (S)—N-(3-((1-(2-((2-hydroxypropyl)amino)pyrimidin-4-yl)-1H-imidazol-2-yl)methyl)phenyl)isonicotinamide,
(S)—N-(3-((1-(2-((2-hydroxypropyl)amino)pyrimidin-4-yl)-1H-imidazol-2-yl)methyl)phenyl)-1H-benzo[d][1,2,3]triazole-5-carboxamide,
(S)-2-([1,1'-biphenyl]-4-yl)-N-(3-((1-(2-((2-hydroxypropyl)amino)pyrimidin-4-yl)-1H-imidazol-2-yl)methyl)phenyl)acetamide,
(S)—N-(3-((1-(2-((2-hydroxypropyl)amino)pyrimidin-4-yl)-1H-imidazol-2-yl)methyl)phenyl)-[1,1'-biphenyl]-4-carboxamide,
(S)—N-(3-((1-(2-((2-hydroxypropyl)amino)pyrimidin-4-yl)-1H-imidazol-2-yl)methyl)phenyl)-[1,1'-biphenyl]-2-carboxamide,
(S)-1-acetyl-N-(3-((1-(2-((2-hydroxypropyl)amino)pyrimidin-4-yl)-1H-imidazol-2-yl)methyl)phenyl)piperidine-4-carboxamide,
(S)-2-((2-cyanophenyl)thio)-N-(3-((1-(2-((2-hydroxypropyl)amino)pyrimidin-4-yl)-1H-imidazol-2-yl)methyl)phenyl)benzamide,
(R)-6-hydroxy-N-(3-((1-(2-(((S)-2-hydroxypropyl)amino)pyrimidin-4-yl)-1H-imidazol-2-yl)methyl)phenyl)-2,5,7,8-tetramethylchromane-2-carboxamide,
(S)-2-chloro-5-(4-chlorobenzyl)-N-(3-((1-(2-((2-hydroxypropyl)amino)-pyrimidin-4-yl)-1H-imidazol-2-yl)methyl)phenyl)benzamide,
(S)-2,2-bis(4-chlorophenyl)-N-(3-((1-(2-(2-hydroxypropylamino)pyrimidin-4-yl)-1H-imidazol-2-yl)methyl)phenyl)acetamide,
(S)—N-(3-((1-(2-((2-hydroxypropyl)amino)pyrimidin-4-yl)-1H-imidazol-2-yl)methyl)phenyl)-3-morpholino-2-(trifluoromethyl)benzamide,
(S)-4-chloro-N-(3-((1-(2-((2-hydroxypropyl)amino)pyrimidin-4-yl)-1H-imidazol-2-yl)methyl)phenyl)-3-(trifluoromethyl)benzamide,
(S)—N-(3-((1-(2-((2-hydroxypropyl)amino)pyrimidin-4-yl)-1H-imidazol-2-yl)methyl)phenyl)-3-morpholino-5-(trifluoromethyl)benzamide,
(S)-1-(3-chlorophenyl)-3-(3-((1-(2-((2-hydroxypropyl)amino)pyrimidin-4-yl)-1H-imidazol-2-yl)methyl)phenyl)urea,
(S)-1-(3,4-dichlorophenyl)-3-(3-((1-(2-((2-hydroxypropyl)amino)pyrimidin-4-yl)-1H-imidazol-2-yl)methyl)phenyl)urea,
(S)-1-(3-chloro-4-(trifluoromethyl)phenyl)-3-(3-((1-(2-((2-hydroxypropyl)amino)pyrimidin-4-yl)-1H-imidazol-2-yl)methyl)phenyl)urea,
(S)-1-(3-((4-ethylpiperazin-1-yl)methyl)-5-(trifluoromethyl)phenyl)-3-(3-((1-(2-((2-hydroxypropyl)amino)pyrimidin-4-yl)-1H-imidazol-2-yl)methyl)phenyl)urea,
(S)—N-(3-(1-(2-((2-hydroxypropyl)amino)pyrimidin-4-yl)-1H-imidazole-2-carbonyl)phenyl)-3-(trifluoromethyl)benzamide,
(S)—N-(3-(1-(2-((2-hydroxypropyl)amino)pyrimidin-4-yl)-1H-imidazole-2-carbonyl)phenyl)-5-(4-methoxyphenyl)furan-2-carboxamide,
(S)—N-(3-(1-(2-((2-hydroxypropyl)amino)pyrimidin-4-yl)-1H-imidazole-2-carbonyl)phenyl)-3-morpholino-5-(trifluoromethyl)benzamide,
(S)—N-(3-(1-(2-((2-hydroxypropyl)amino)pyrimidin-4-yl)-1H-imidazole-2-carbonyl)phenyl)-3-(4-methylpiperazin-1-yl)-5-(trifluoromethyl)benzamide,
(S)-4-chloro-N-(3-(1-(2-((2-hydroxypropyl)amino)pyrimidin-4-yl)-1H-imidazole-2-carbonyl)phenyl)benzamide,
(S)-3-chloro-N-(3-(1-(2-((2-hydroxypropyl)amino)pyrimidin-4-yl)-1H-imidazole-2-carbonyl)phenyl)benzamide,
(S)-1-(3,4-dichlorophenyl)-3-(3-(1-(2-((2-hydroxypropyl)amino)pyrimidin-4-yl)-1H-imidazole-2-carbonyl)phenyl)urea,
(S)-1-(4-chlorophenyl)-3-(3-(1-(2-((2-hydroxypropyl)amino)pyrimidin-4-yl)-1H-imidazole-2-carbonyl)phenyl)urea,
(S)-4-chloro-N-(4-(1-(2-((2-hydroxypropyl)amino)pyrimidin-4-yl)-1H-imidazole-2-carbonyl)phenyl)benzamide,
(S)-3-chloro-N-(4-(1-(2-((2-hydroxypropyl)amino)pyrimidin-4-yl)-1H-imidazole-2-carbonyl)phenyl)benzamide,
(S)—N-(4-(1-(2-((2-hydroxypropyl)amino)pyrimidin-4-yl)-1H-imidazole-2-carbonyl)phenyl)-3-morpholino-5-(trifluoromethyl)benzamide,
(S)-4-chloro-N-(4-(1-(2-((2-hydroxypropyl)amino)pyrimidin-4-yl)-1H-imidazole-2-carbonyl)phenyl)-3-(trifluoromethyl)benzamide,
(S)—N-(4-(1-(2-((2-hydroxypropyl)amino)pyrimidin-4-yl)-1H-imidazole-2-carbonyl)phenyl)-3-(4-methylpiperazin-1-yl)-5-(trifluoromethyl)benzamide,
(S)-1-(4-chloro-3-(trifluoromethyl)phenyl)-3-(4-(1-(2-((2-hydroxypropyl)amino)pyrimidin-4-yl)-1H-imidazole-2-carbonyl)phenyl)urea, and
(S)-1-(3,4-dichlorophenyl)-3-(4-(1-(2-((2-hydroxypropyl)amino)pyrimidin-4-yl)-1H-imidazole-2-carbonyl)phenyl)urea.

4. A pharmaceutical composition for treating melanoma or leukemia, comprising the imidazole-1-yl pyrimidine derivative, or the pharmaceutically acceptable salt thereof according to claim 1 as an active ingredient.

5. The pharmaceutical composition for treating melanoma or leukemia according to claim 4, inhibiting the proliferation of abnormal cell by inhibiting protein kinas which is one or more selected from the group consisting of BRAF, BRAF mutants, and CRAF.

6. The pharmaceutical composition according to claim 4, showing the antiproliferative activity to A375P human melanoma cell line or U937 human leukemic monocyte lymphoma cell line.

* * * * *